United States Patent [19]

McDougall

[11] Patent Number: 4,652,265

[45] Date of Patent: Mar. 24, 1987

[54] IMPLANTABLE BLOOD PUMP AND INTEGRAL APPARATUS FOR THE OPERATION THEREOF

[76] Inventor: David A. McDougall, C. P. 311, Ste-Agathe, Quebec, Canada, J8C 3C6

[21] Appl. No.: 422,295

[22] Filed: Sep. 23, 1982

[51] Int. Cl.[4] .......................... A61F 2/22; A61F 2/08; A61F 2/72

[52] U.S. Cl. ........................................ 623/3; 623/14; 623/24; 623/26; 128/1 D

[58] Field of Search .................... 3/1.7, 1–1.2, 3/1.9, 1.91; 128/1 D; 623/3, 11, 13, 14, 24–26

[56] References Cited

U.S. PATENT DOCUMENTS

| | | | |
|---|---|---|---|
| 3,434,162 | 3/1969 | Wolfe | 3/1.7 |
| 3,771,173 | 11/1973 | Lamb, Jr. | 3/1.7 |
| 4,023,468 | 5/1977 | Poirier | 128/1 D X |
| 4,051,840 | 10/1977 | Kantrowitz et al. | 3/1.7 X |
| 4,453,537 | 6/1984 | Spitzer | 3/1.7 X |

Primary Examiner—Ronald L. Frinks

[57] ABSTRACT

A blood pump is powered by an implantable motive power source. The blood pump has four actively pumping chambers, two of the chambers simulating ventricles and two of the chambers simulating atria, wherein the ventricular and atrial chambers are driven in a reciprocating manner by a pivoting wedge hinged to a septal wall partition separating the ventricular from the atrial chambers. The pivoting wedge is hydraulically powered through systole and diastole by means of hydraulic motors harnessed individually to respective skeletal muscles and responsive to the contraction of these muscles which are sequentially contracted by control stimulation means. The hydraulic pressure from the hydraulic motors is transmitted through hydraulic lines to the blood pump.

15 Claims, 36 Drawing Figures

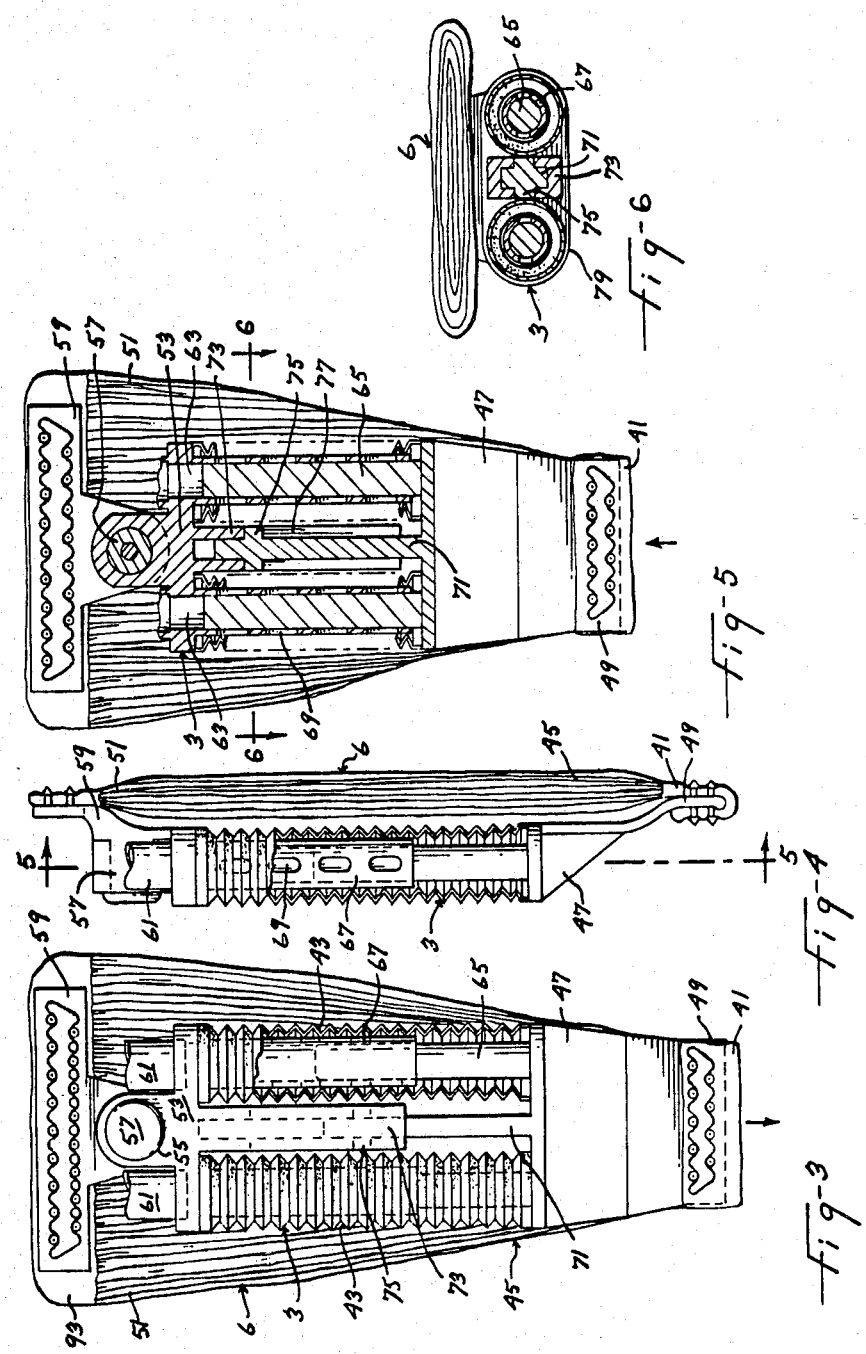

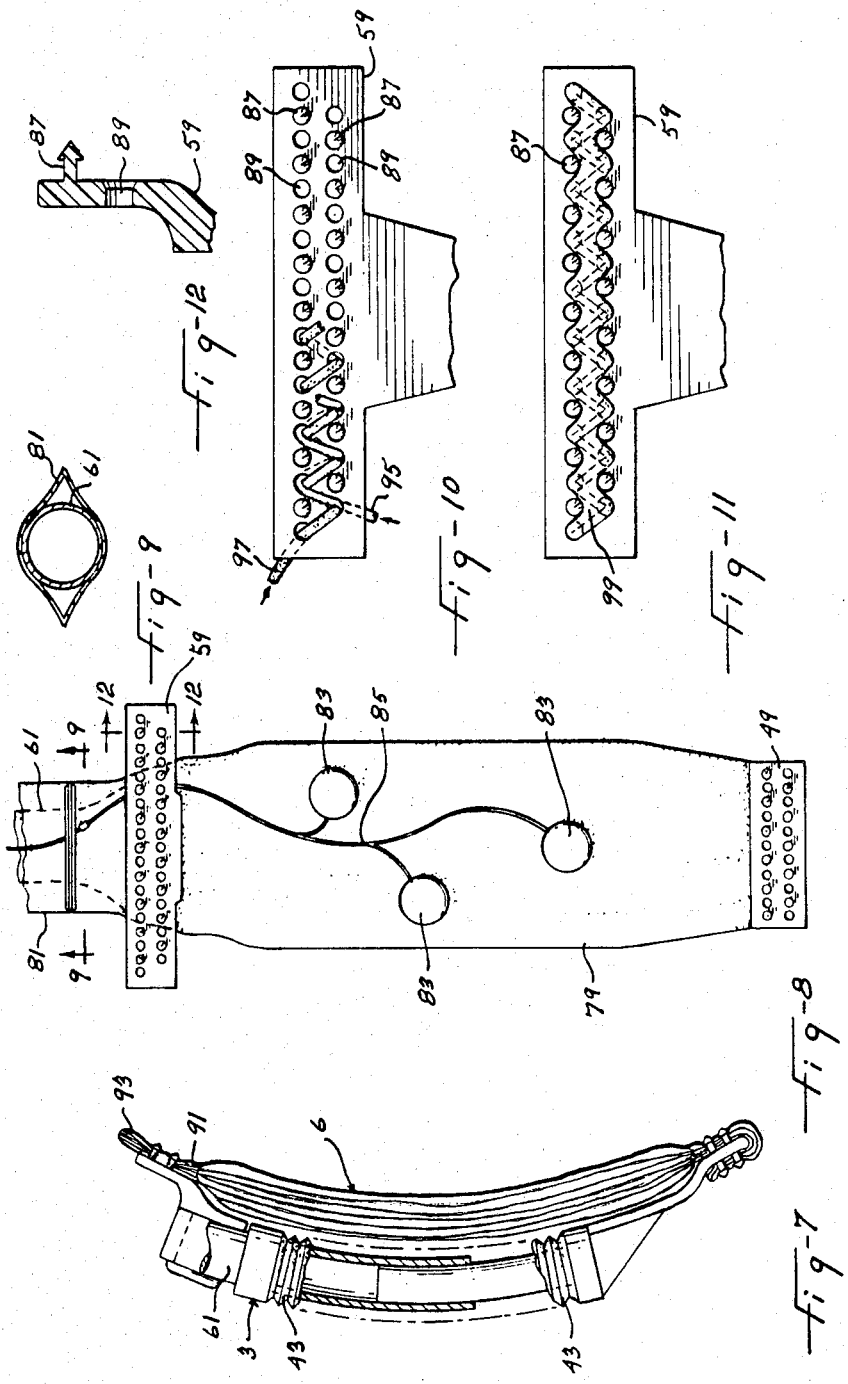

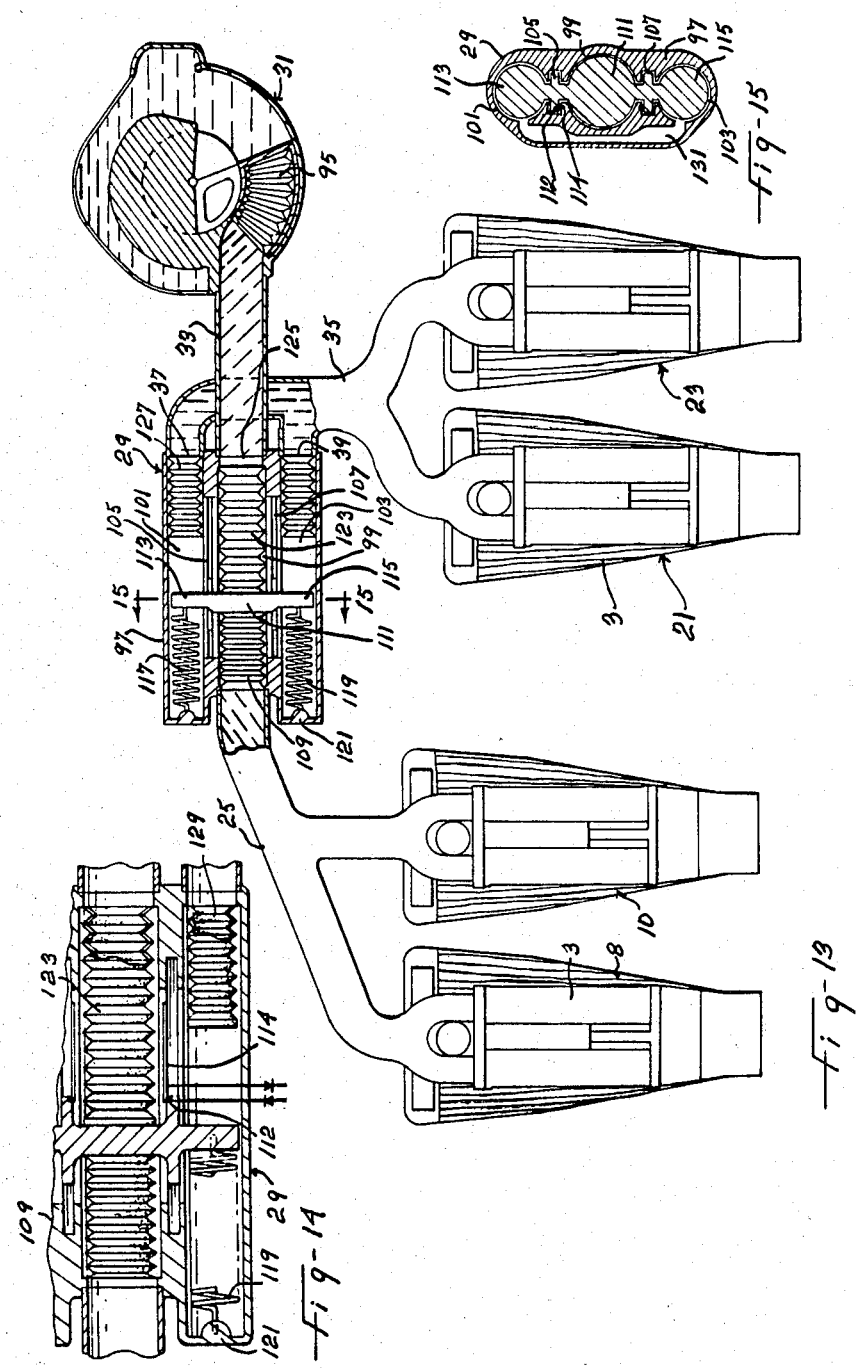

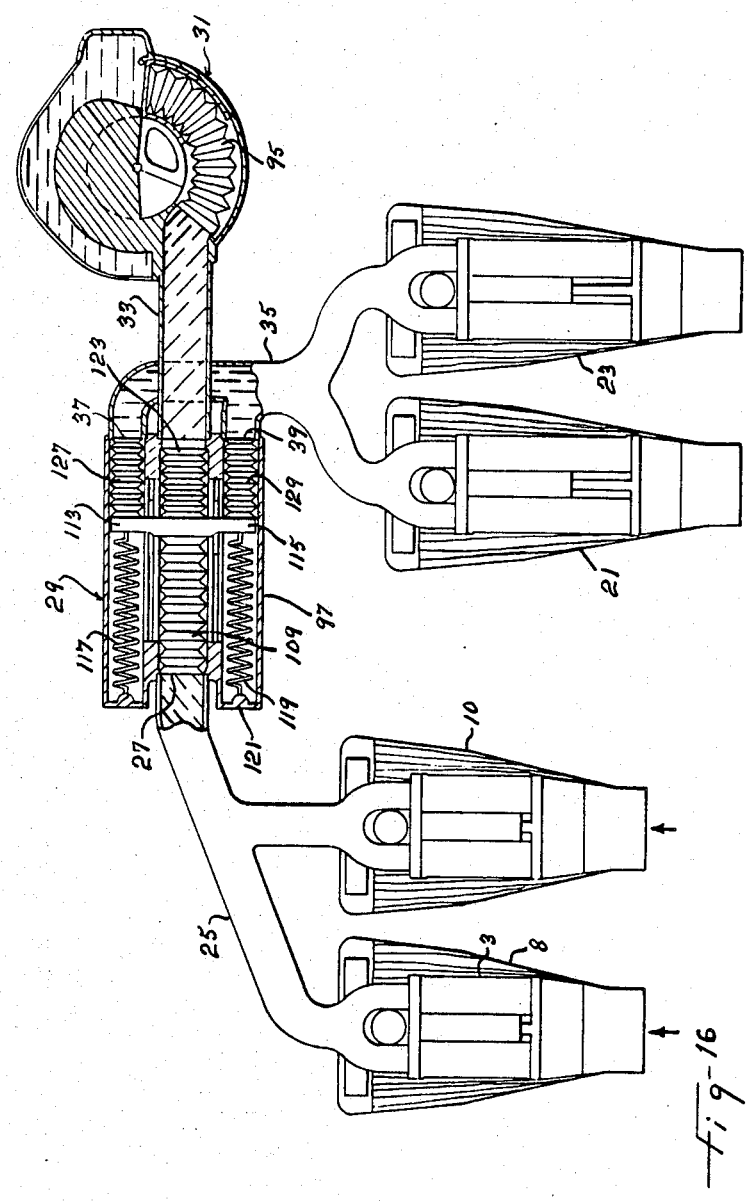

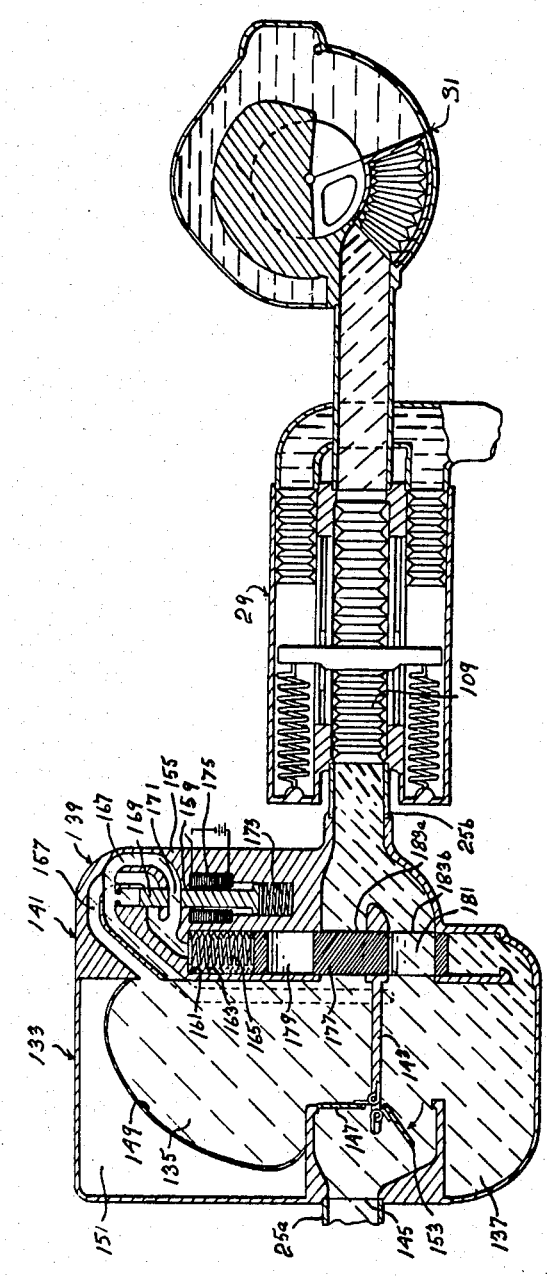

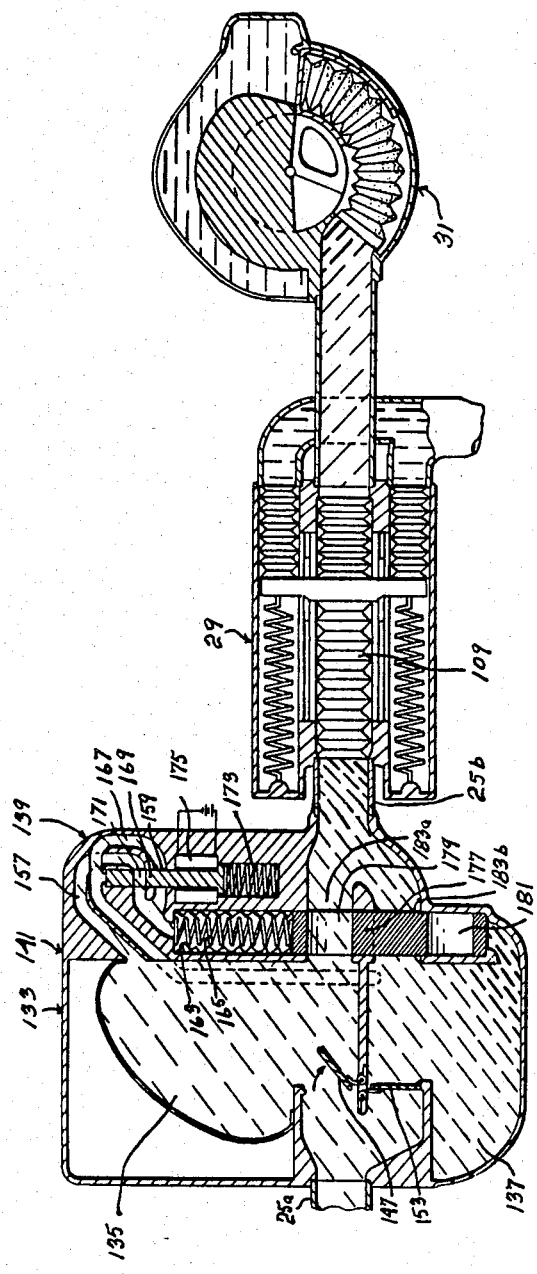

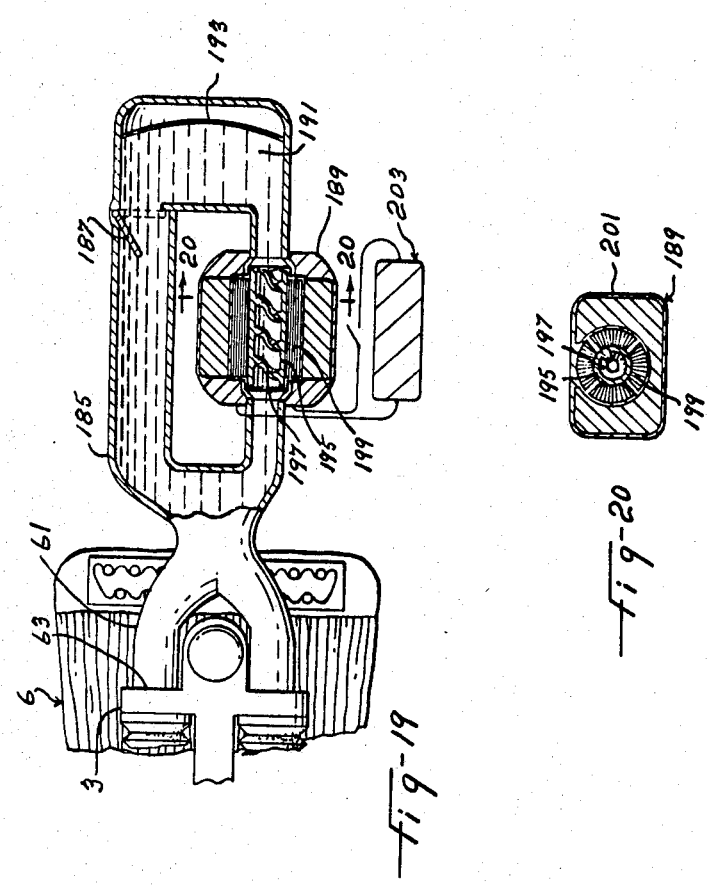

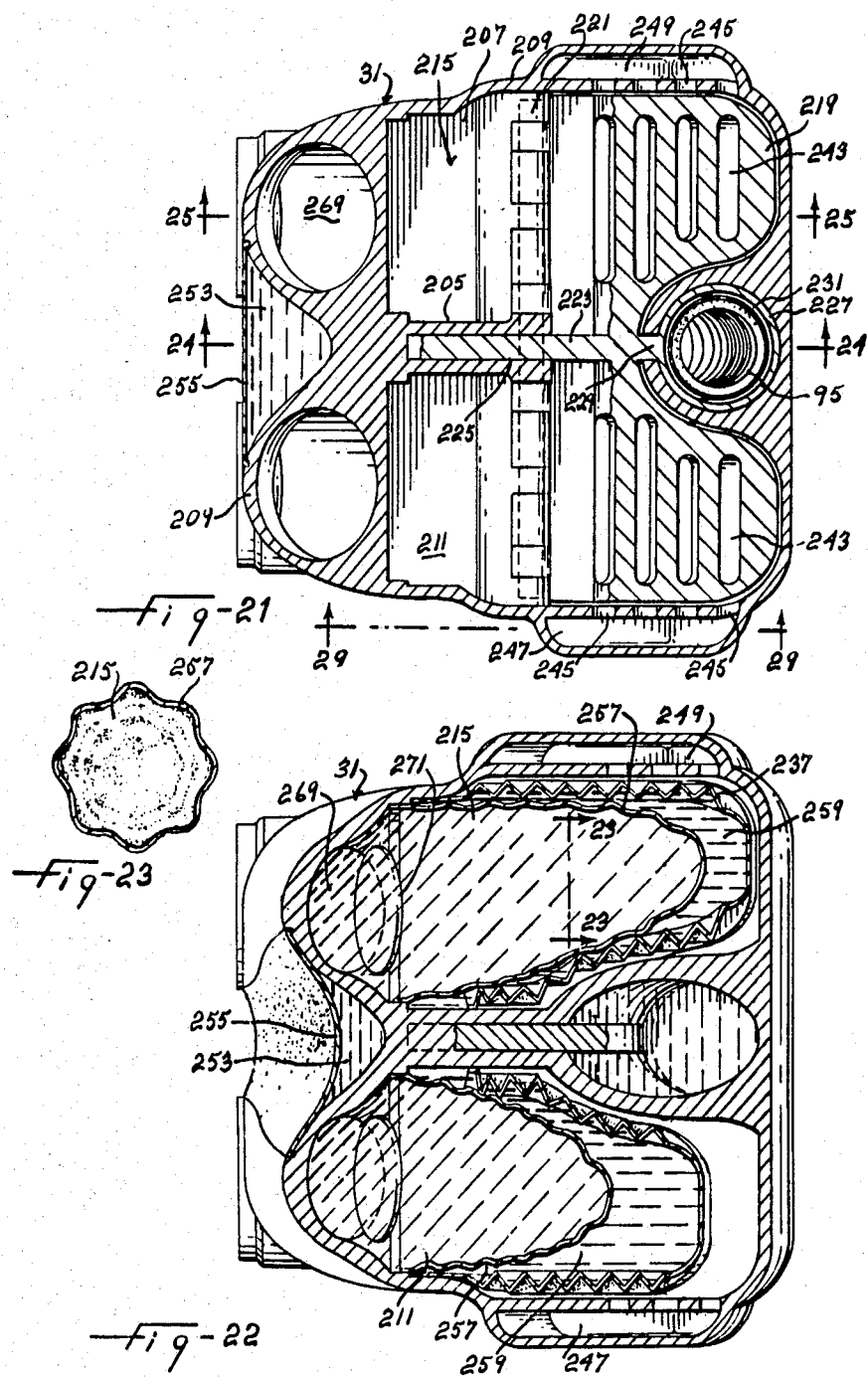

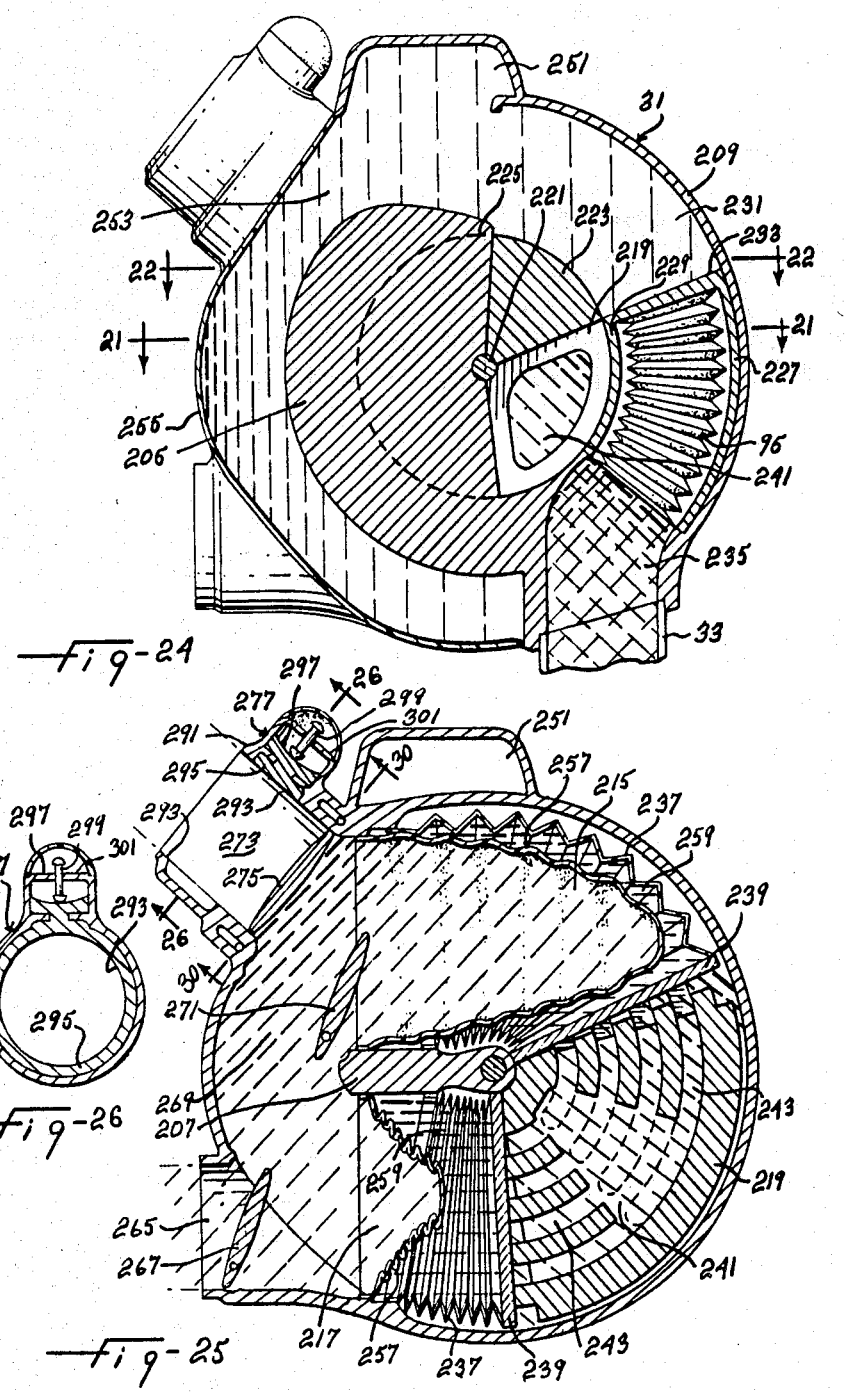

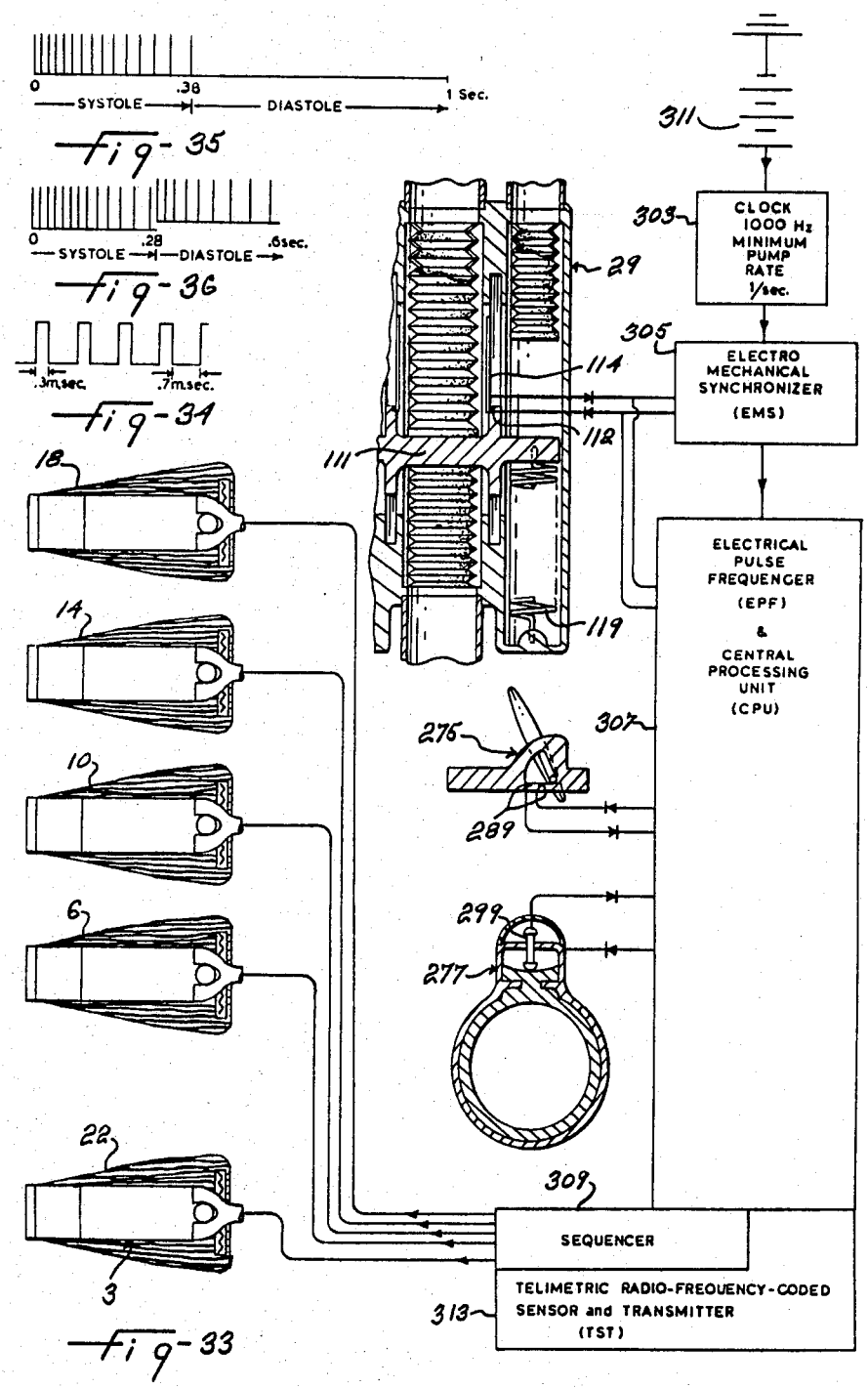

IMPLANTABLE BLOOD PUMP AND INTEGRAL APPARATUS FOR THE OPERATION THEREOF

BACKGROUND OF THE INVENTION

1. Field of the Invention

The invention relates to a heart replacement system for use in experimental animals and, ultimately, in the human body. More specifically, the invention relates to such a system which includes a pump means and elements for driving the pump means, the elements being attached to skeletal muscles and being actuable by sequential stimulated contraction of skeletal muscles.

2. Description of the Prior Art

The search for an implantable heart replacement system to replace a diseased heart no longer capable of sustaining life despite optimal medical or surgical intervention has identified the following requirements—an implantable power source for a blood pump; an implantable blood pump capable of reproducing the pump functions of the natural heart; and a control system for altering the performance of the blood pump in response to body needs.

Approaches to an implantable power source have included nuclear isotopes providing thermal power and batteries storing electrical power. (Ref.—Artificial Heart Driving Systems—Historical Review and Future Possibilities, Mrava GL, Adv. Biomed. Eng. Med. Phys. 3:31-68, 1970; Power Systems for Artificial Hearts, pp. 922-36, Mohnhaupt. R. et al, in Hwang NH, Normann NA, ed. Cardiovascular Flow Dynamics and Measurements, Baltimore, Univ. Park Press 1977 WG 106 N 111c 1975; U.S. Pat. No. 4,058,857, 1977, Runge et al; and U.S. Pat. No. 4,221,548, 1980, Child.) The nuclear power approach has been limited by problems of heat dissipation and radiation poisoning. The electric battery approach has been limited by the need for frequent recharging.

Skeletal muscle has been used in various methods to augment the performance of the natural, diseased heart. (Ref.—Macoviak J.A., Surgical Forum 1980, pp. 270-271, vol. XXXI; Drinkwater, D.C., Surgical Forum 1980, pp. 271-274, vol. XXXI). The methods described involve repositioning of skeletal muscle from its original anatomic location to a position on the wall of the natural heart or a vessel arising from the heart. These methods are limited by the fibrosing tissue response to repositioning of the muscle which compromises the contractile performance of the repositioned muscle, by the difficulty in protecting the blood supply of the repositioned muscle, and by the physiologic differences between skeletal muscle and heart muscle, skeletal muscle being more fatiguable than a comparable amount of heart muscle.

Multichannel skeletal muscle stimulators have been developed for artificial electrical stimulation of skeletal muscles in the limbs of paraplegic patients to restore the ability to walk, and in the backs of children with scoliosis to effect a correction of the skeletal deformity. (Ref.—Stroznik, P., IEEE Transactions on Biomedical Engineering, vol. BME—26, No. 2, Feb. 1979, pp. 112-116; Hralj, A., Med. Progress Technol., 7, 1980, pp. 3-9; Axelgaard, J., Orthop. Trans. 4, 29-30, 1980.) In these methods, artificial activation of the skeletal muscles causes a locomotory or postural effect similar to that resulting from natural activation of the muscles.

Approaches to an implantable blood pump capable of reproducing the pump functions of the natural heart are varied. One approach has been to incorporate a large passive chamber, simulating the natural atrium, between each active ventricle chamber and the vein from which blood is drawn into the ventricle chamber during diastole. This approach is intended to reduce the deleterious suction effect causing collapse of the vein during diastole and thereby limiting filling of the ventricle. (Ref.—Nosé Y., Trans. Amer. Soc. Artif. Int. Organs. 1966, vol. XII, pp. 301-311). This approach is limited by sludging of blood in the large atrial chamber, predisposing the blood to clotting.

Other approaches have been directed to minimizing destruction of blood elements by using a pneumatically activated polyurethane membrane to pressurize blood in the artificial ventricle. (Ref.—Hessler, T. R., Trans. Am. Soc. Artif. Intern. Organs. vol. XXIV, 1978, pp. 532-536). While polyurethane does have suitable blood contacting properties, the noncorrugated design of the membrane necessitates a large diameter membrane in order to effect a suitable blood stroke volume. Blood pumps with such a large diameter membrane have been limited by blood stagnation at the periphery of the membrane.

Other approaches in blood pump design provide inherent control of blood stroke volume by venous filling pressure. (Ref.—Kwan-Gett, C. S., Trans. Am. Soc. Artif. Int. Organs., 1969, vol. XV, pp. 245-266; Pierce, W. S., Surgery, Aug. 1981, pp. 137-147). In these designs, each half of the blood pump acts independently of the other half in its response to changes in venous filling pressure.

Various control systems have been described for altering the cycling rate of an implantable blood pump in response to changing perfusion requirements of the body. Some systems rely on measurement of left atrial pressure and aortic pressure by fluid filled catheters connected to remote transducers. Other systems are described which relate to blood pumps powered pneumatically by an external air pump. These systems rely on deriving left atrial and aortic pressures from analysis of the air pressure wave driving the blood pump. (Ref.—Landis, D. L., Trans. Am. Soc. Artif. Intern. Organs., 1977, vol. XXIII, pp. 519-525; and U.S. Pat. No. 4,086,653, 1978, Gernes).

SUMMARY OF THE INVENTION

It is an objective of the invention to provide an implantable heart replacement system, comprising an implantable power source, an implantable blood pump and an implantable control system, which overcomes the limitations of prior designs.

The invention is directed to an implantable motive power apparatus for operating an artificial replacement muscle comprising means for harnessing the contractile force of one or more skeletal muscles while the skeletal muscles remain in their anatomic bed, and means for transmitting the motive power to the artificial replacement muscle for operating the artificial muscle in a manner simulating the operation of the muscle it is replacing.

It is a more specific objective of the invention to provide an implantable power source that will perpetually power a blood pump. The power source comprises mechanisms for harnessing the contractile force of a plurality of skeletal muscles. The muscles harnessed to the mechanisms are stimulated artificially to contract in a sequence, so that while one muscle or one muscle pair may be contracting, the other muscles are resting. By employing several sequentially stimulated muscles, the resting interval between subsequent contractions of any individual muscle can be sufficiently long to prevent fatigue in that muscle.

It is a more specific objective of the invention to provide such a power source wherein the mechanism for harnessing the contractile force of skeletal muscle does not require repositioning of the muscle from its anatomic bed or disturbance of its vascular supply, thus minimizing impairment of the contractile abilities of the muscle.

It is a more specific objective of the invention to provide such a power source wherein the contractile force of skeletal muscles is harnessed as hydraulic pressure, such that the hydraulic pressure generated from contraction of a harnessed skeletal muscle or pair of muscles is transmitted through hydraulic lines to power one systolic stroke of the blood pump.

It is an alternative objective of the invention to provide such a system wherein the hydraulic pressure from harnessed muscle contraction is stored in a reservoir which is activated by a solenoid switch to release hydraulic fluid to cause one systolic stroke. In this alternative, the speed of harnessed muscle contraction may be slower than the systolic strmke speed of the blood pump.

It is a further alternative objective to provide such a system wherein the hydraulic pressure from harnessed muscle contraction may be converted into electrical current transmitted by electrical wiring to a battery supplying the pacing apparatus which stimulates the harnessed muscles.

It is a further objective of the invention to provide a means for firmly mounting the harnessing mechanism on pkeletal muscle.

It is an alternative consideration of the invention that the mechanism for harnessing the contractile force of a skeletal muscle may be used to remotely power devices other than a blood pump, such as an implantable prosthetic muscle in the form of a hydraulically actuated strut acting across a joint.

It is a further objective of the invention to provide a heart replacement system which includes a blood pump with actively pumping atria to enable venous uptake by the blood pump to occur throughout systole and into diastole, thus improving on the deleterious suction effect on the veins were venous uptake to occur only during diastole and preventing blood stagnation in an artificial chamber which might occur with non-pumping artificial atria. While venous uptake may occur in both systole and diastole, ejection of blood by the pump into the arteries occurs only during systole and is thus pulsatile.

It is a further objective to provide a blood pump with four actively pumping chambers, two of the chambers simulating ventricles and two of the chambers simulating atria, wherein the ventricular and atrial chambers are driven reciprocatively by one hydraulically powered wedge hinged to the septal wall separating ventricular from atrial chambers.

It is a further objective to provide a blood pump with a mechanism comprising a fluid cushion and a conical, two-way corrugated blood sac in each pump chamber. This mechanism is intended to provide specific blood flow characteristics within the blood sac.

It is a further objective to provide a blood pump with a mechanism that dampens and prolongs the pressure exerted by the blood pump on the veins supplying the pump. This mechanism comprises in part a fluid reservoir connected to a fluid interspace between driving wedge and fluid cushion in each pump chamber.

It is a further objective of the invention to provide a blood pump with a mechanism that responds to conditions of reduced venous pressure affecting one or both halves of the blood pump by reducing the stroke volume of the one or both halves, respectively, of the blood pump. This mechanism comprises in part the fluid reservoir and fluid interspaces mentioned above.

It is a further objective to provide a blood pump with a mechanism that responds to a discrepancy in blood pressure between the veins supplying the left and right halves of the blood pump by decreasing the stroke volume of that half of the pump experiencing the lower venous pressure and by increasing the stroke volume of that half of the pump experiencing the higher venous pressure.

It is a further objective of the invention to provide an implantable electronic muscle stimulation and blood pump control system that will automatically regulate the pump cycle rate in response to varying perfusion requirements of the body during rest and exercise. The electronic control system comprises in part a sensor of aortic pressure and a novel mechanism for indirectly sensing left-sided venous pressure.

Other features and objectives of the invention will be described in, or become apparent from, a reading of the following text.

BRIEF DESCRIPTION OF THE DRAWINGS

FIG. 3 is a top view of a muscle to which a hydraulic pump-drive unit is mounted, the muscle shown at its relaxed, extended length, the hydraulic pump-drive unit shown partially in section;

FIG. 4 is a side view, partially in section, of the elements shown in FIG. 3;

FIG. 5 is a top view similar to FIG. 3 showing the pump-drive unit in longitudinal cross-section, taken through line 5—5 of FIG. 4 and with the muscle in its contracted condition;

FIG. 6 is a lateral cross-section taken through line 6—6 of FIG. 5;

FIG. 7 is a side view similar to FIG. 4 but illustrating a hydraulic pump-drive unit of a curved design to fit a curved body-wall contour;

FIG. 8 is a bottom view of the pump-drive unit without the muscle and showing a typical envelope surrounding the unit;

FIG. 9 is a lateral cross-section taken along line 9—9 of FIG. 8;

FIGS. 10 and 11 are enlarged plan views illustrating the means for attaching the ends of the pump-drive unit to a tendon;

FIG. 12 is an enlarged plan view taken through line 12—12 of FIG. 8;

FIG. 13 is a schematic plan illustrating two pairs of skeletal muscles harnessed with pump-drive units, a systolic-diastolic actuator, a blood pump, and hydraulic lines connecting the above elements as illustrated. Both pairs of muscles are shown at their relaxed, extended length, and the blood pump is shown in its end-diastolic appearance;

FIG. 14 is an enlarged view of the systolic-diastolic actuator in longitudinal cross-section;

FIG. 15 is a lateral cross-section of the systolic-diastolic actuator taken through line 15—15 of FIG. 13;

FIG. 16 is a schematic plan similar to FIG. 13 showing one pair of muscles contracted and the blood pump in its end-systolic appearance;

FIG. 17 is a schematic diagram of an alternative embodiment wherein a hydraulic pressure reservoir unit is inserted in the hydraulic line between the pump drive units (not shown) and systolic-diastolic actuator. The pressure reservoir unit, systolic-diastolic actuator and blood pump are shown in their respective end-diastolic appearances;

FIG. 18 is a schematic diagram similar to FIG. 17 showing the pressure reservoir unit, systolic-diastolic actuator and blood pump in their respective end-systolic appearances;

FIG. 19 is a schematic diagram of another embodiment wherein a pump-drive unit is hydraulically connected to a dynamo;

FIG. 20 is a cross-sectional view of the dynamo taken through line 20—20 of FIG. 19;

FIG. 21 is a cross-sectional view of a blood pump in accordance with the present invention, taken through line 21—21 of FIG. 24;

FIG. 22 is a cross-sectional view of the blood pump taken through line 22—22 of FIG. 24;

FIG. 23 is a cross-sectional view of a blood sac taken through line 23—23 of FIG. 22;

FIG. 24 is a cross-sectional view of the blood pump taken through line 24—24 of FIG. 21, the blood pump being shown in its end-diastolic appearance;

FIG. 25 is a cross-sectional view of the blood pump taken through line 25—25 of FIG. 21, the blood pump being shown in its end-diastolic appearance;

FIG. 26 is a cross-sectional view of an aortic pressure transducer taken through line 26—26 of FIG. 25;

FIG. 33 is a block diagram of the electronic muscle-stimulation and blood pump-control system;

FIG. 34 is a diagram of the electric pulse pattern produced by the clock of the system illustrated in FIG. 33;

FIG. 35 is a diagram of an electric pulse pattern produced by the pulse frequencer of the system illustrated in FIG. 33; and FIG. 36 is a diagram of an alternate electric pulse pattern produced by the pulse frequencer.

DESCRIPTION OF THE PREFERRED EMBODIMENTS

Figure 1:
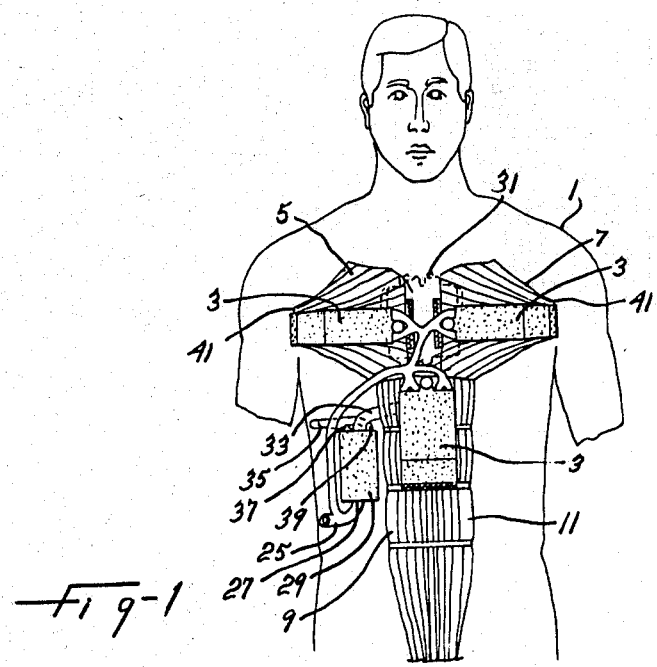
FIG. 1 is a schematic view of the front of a human subject illustrating hydraulic pump-drive units attached to various skeletal muscles.
Figure 2:
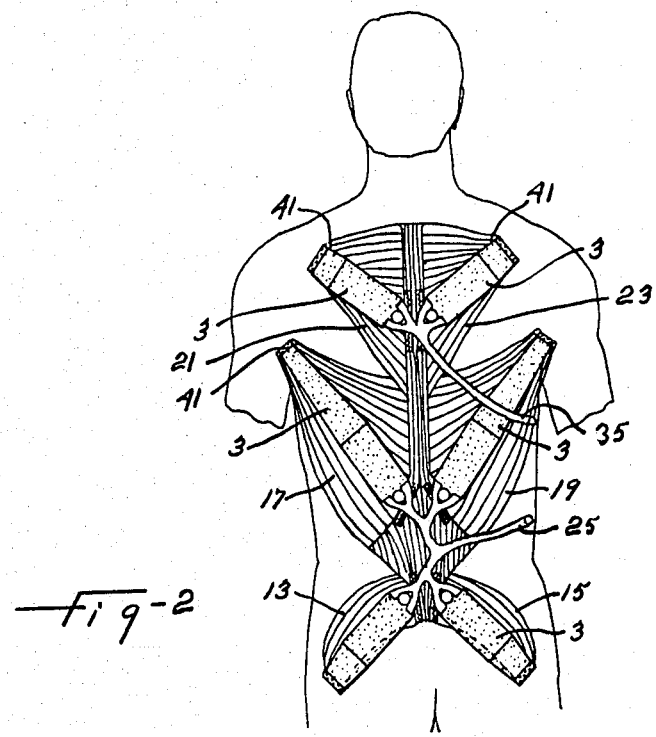
FIG. 2 is a schematic view similar to FIG. 1 but of the back of a human subject.
Figure 27:
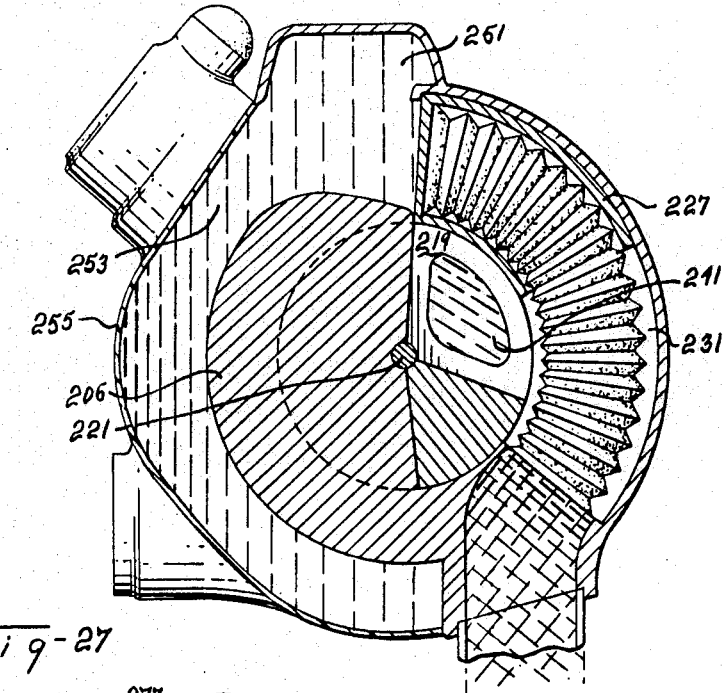
FIG. 27 is a cross-sectional view similar to FIG. 24, showing the blood pump in its end-systolic appearance.

Referring to FIGS. 1 and 2, these Figures illustrate a subject 1 having a plurality of pump-drive units 3 harnessed to skeletal muscles 5, 7, 9, 11, 13, 15, 17, 19, 21 and 23 of the subject. Units 3 are harnessed on the right and left halves of the Pectoralis Major muscle pair 5 and 7, on the superior parts of the right and left halves of the Rectus Abdominis muscle pair 9 and 11, on the superior parts of the left and right halves of the Gluteus Maximus muscle pair 13 and 15, on the left and right halves of the Latissimus Dorsi muscle pair 17 and 19, and on the middle and inferior parts of the left and right halves of the Trapezius muscle pair 21 and 23.

The harnessed skeletal muscles 5 through 19 are connected by the hydraulic branch line 25, surgically burred in the subcutaneous tissue of the subject, to the systolic inlet 27 of a systolic-diastolic actuator 29, which is itself connected to a mediastinal blood pump 31 by hydraulic line 33. The hydraulic line 33 is surgically tunnelled beneath the Rectus Abdominis muscle pair 9 and 11 and through a surgically formed hole in the anterior midline aspect of the diaphragm in its route to the blood pump 31.

The harnessed skeletal muscles of the Trapezius pair 21 and 23 are connected by hydraulic line 35 to the diastolic ports 37 and 39 of the systolic-diastolic actuator 29.

The pump-drive units 3 are surgically positioned in the tissue overlying the muscle bellies of the skeletal muscles 5 through 23, and as described below, each unit 3 is firmly attached to the origin and insertion tendons of each muscle. The anatomic position of each harnessed muscle is not altered, and the tissue deep to each harnessed muscle, containing the vascular supply to the muscle, is not disturbed.

The natural motor nerves of the harnessed muscles 5 through 23 are surgically interrupted so that these muscles will contract only when electrically stimulated by the pacing apparatus to be described below. The insertion tendons 41 of the harnessed muscles are severed so that contraction of these muscles will no longer effect the natural locomotory or postural changes. To preserve the integrity of the abdominal wall, the tendinous inscription of the Rectus Abdominis muscle pair 9 and 11 may be left unsevered if the inferior halves of the Rectus pair are denervated.

The harnessed skeletal muscles 5 through 23 may be considered expendable in that the loss of their natural locomotory or postural functions may be at least partially compensated by surrounding muscles.

As will become evident from a further reading of the text, artificially stimulated contraction of each of the four muscle pairs 5 and 7, 9 and 11, 13 and 15, and 17 and 19, will effect one systolic stroke of the blood pump. Each muscle pair contracts in a sequence with the other three muscle pairs so that each muscle pair contracts for only one of four consecutive systolic strokes of the blood pump. In this manner, fatigue in any one muscle pair is avoided. The contraction strength of each harnessed muscle pair is greater than 100 pounds, which is more than twice the strength required to power the blood pump.

As will be described further on in the text, artificially stimulated contraction of the harnessed muscle pair 21 and 23 assists the systolic-diastolic actuator 29 in effecting one diastolic stroke of the blood pump.

Referring now to FIGS. 3 to 12, various aspects of a representative pump-drive unit 3 mounted on a representative skeletal muscle 6 will be described.

The pump-drive unit 3 includes a pair of identical bellows 43 extending longitudinally and parallel to the axis of contraction of the underlying skeletal muscle 6. At the insertion end 45 of muscle 6, the bellows 43 are firmly attached to a base member 47 which includes an anchor plate 49 for attaching the base member 47 to the severed insertion tendon 41 of muscle 6. At the origin end 51 of muscle 6, the bellows 43 are attached to a head member 53 which includes a cylindrical hole 55 for pivotal attachment of the head member 53 to a cylindrical projection 57 of anchor plate 59. The pivotal attachment of the head member 53 to the anchor plate 59 permits rotation of the pump-drive unit 3 around the axis of the cylindrical projection 57 during locomotory or respiratory movements of the surrounding tissues.

Inside each bellows 43 is contained a hydraulic fluid, preferably an alcohol, which communicates with hydraulic fluid in the hydraulic line 61 via outlets 63 in the head member 53.

Inside each bellows 43 are a piston 65 attached to the base member 47 and a cylinder 67 attached to the head member 53. The cylinder 67 has fenestrations 69 for passage of hydraulic fluid between the bellows 43 and the interior of the cylinder 67. The piston 65 projects into the cylinder 67 as illustrated. The piston-cylinder assembly acts as a guide for the bellows 43 during contraction of the bellows.

A stem 71 extends from the base member 47 between the bellows 43 and slides in a box-shaped extension 73 of head member 53. The stem 71 includes lateral projections 75 which slide in lateral slots 77 of extension 73. The purpose of the projections 75 in slots 77 is to limit the travel of the stroke of the pump drive unit.

The bellows 43 are sealed with the exception of the outlets 63 connecting the bellows with the hydraulic line 61. The bellows 43 are made of a suitable construction to prevent lateral expansion. For example, steel rings may form the peaks of the corrugations, or the bellows may be formed in a spiral corrugation using a coiled spring, the normal shape of which would be the extended position of the bellows.

Referring to FIGS. 6, 8 and 9, the pump-drive unit 3 is contained in a flexible envelope 79 made of a biocompatible material such as polyurethane. The envelope 79 is sealed around the anchor plates 49 and 59 so that the anchor plates extend outside the envelope 79. The envelope 79 is attached to a similar envelope 81 surrounding the hydraulic line 61. Contained within the envelopes 79 and 81, between the envelope and pump-drive unit or hydraulic line respectively, is a suitable fluid medium sealed within the envelopes. The purpose of envelope 79 enclosing pump-drive unit 3 is to prevent body tissue elements from encroaching onto, and interfering with, the components of the pump-drive unit. The purpose of envelope 81 enclosing the hydraulic line 61 is to permit movement of the hydraulic line within the envelope against the body wall during locomotory or respiratory movements, the hydraulic line having slack within the envelope 81.

Referring to FIG. 8, embedded in the surface of the envelope 79, on the side of the envelope which will be in contact with the muscle, are provided a plurality of electrodes 83, of suitable material such as hydron-coated tantalum or activated carbon, connected by insulated wiring 85 to an electronic stimulating unit described further on.

Referring to FIGS. 10, 11 and 12, the anchor plate 59 includes projections in the form of anchor pins 87 alternating in a staggered triangular pattern with openings 89 in the anchor plate 59. The anchor pins 87 have cone-shaped tips with the bottom of the cone having a larger diameter than the stem of the pin, so that the anchor pin hooks into the tendon material 91 (FIG. 7) when the anchor plate 59 is pressed onto the tendon 93. Two sutures 95 and 97 are then run through the tendon 93 and through the openings 89 in the manner illustrated in FIG. 10. The sutures are preferably of carbon fiber or other absorbable substance which will induce ingrowth of fibrous tissue 99 in the alignment of the suture material. The fibrous tissue 99 will grow through the openings 89 and grow in a zig-zag pattern between the anchor pins 87 as illustrated in FIG. 10, thus securing a firm bond between tendon 93 and the anchor plate 59. The orientation of the zig-zag fibrous tissue pattern is approximately perpendicular to the orientation of the natural tendon fibers 91 of tendon 93.

In the embodiment shown in FIGS. 3 and 4, the severed insertion tendon 41 of muscle 6 has been folded over the end of anchor plate 49, which in this case has anchor pins extending from both sides thereof.

In operation of the pump-drive unit 3, a programmed pulsed current is conducted from an electronic control unit to the muscle 6 via wiring 85 and electrodes 83, stimulating the muscle to contract from its relaxed length shown in FIG. 3 to its contracted length shown in FIG. 5, forcing the insertion tendon 41 and attached base member 47 towards the origin tendon 93 and head member 53, thereby causing compression of the bellows 43 which will force hydraulic fluid within the bellows to be expelled through the outlets 63 into the hydraulic line 61, thus displacing fluid in the hydraulic line 61 into the systolic-diastolic actuator 29 via the systolic inlet 27.

Upon cessation of electrical stimulation, the muscle 6 will relax and will be returned to its precontraction length by a reversal of hydraulic fluid flow effected by the systolic-diastolic actuator, as will be described further on. As previously mentioned, spring devices could be utilized in the bellows 43 or otherwise in the pump-drive unit 3 to aid the extension of the pump-drive unit and attached muscle to the pre-contracted position.

It is anticipated that the pump-drive unit harnessed to a skeletal muscle could be used to power devices other than a blood pump. For example, a pump-drive unit mounted on a Pectoralis Major muscle could power a prosthetic arm muscle in order to provide elbow flexion (or extension) in a subject with a paralyzed arm. The prosthetic arm muscle would comprise a hydraulically actuated strut, attached at both ends to tendon or bone, and positioned across the elbow joint. In this embodiment, the pump-drive unit would be connected to the strut by a hydraulic line tunnelled surgically in the subcutaneous tissue of the chest and arm. Operation of the pump-drive unit by contraction of the Pectoralis muscle would effect a shortening (or lengthening) of the strut, thereby flexing (or extending) the elbow joint. Denervation and artificial stimulation of the Pectoralis muscle would be unnecessary, since the subject could relearn, and voluntarily control, the new function of the Pectoralis muscle.

Referring now to FIGS. 13, 14, 15 and 16, four muscles 8, 10, 21 and 23 are shown with a pump-drive unit 3 attached to each muscle. The pump-drive units of the pair of muscles 8 and 10 are connected by the hydraulic line 25 to the systolic inlet port 27 of the systolic-diastolic actuator 29. The pump-drive units of the pair of muscles 21 and 23 are connected by the hydraulic line 35 to the two diastolic ports 37 and 39 of the systolic-diastolic actuator. The systolic-diastolic actuator 29 is connected by the hydraulic line 33 to the driving bellows 95 of the blood pump 31.

The systolic-diastolic actuator 29 includes a housing 97 through which extends a central longitudinal bore 99 and two parallel satellite bores 101 and 103. Between the satellite bore 101 and the central bore 99 there is a longitudinal slot 105, while a similar slot 107 is provided in the housing between the satellite bore 103 and the central bore 99. The central bore terminates at one end of the housing in the systolic inlet port 27. A bellows 109 extends from the systolic inlet port 27 and is connected to a plunger 111 which is adapted to slide in a portion of the length of the central bore 99. The plunger 111 includes lateral extensions 113 and 115 which extend within the satellite bores 101 and 103 respectively. Within the slots 105 and 107, the plunger includes electrical contact members 112 which are adapted to slide against a plurality of sensor contacts 114 in each of the slots 105 and 107, as shown in enlarged detail in FIGS. 14 and 15. This arrangement allows for electronic sensing of the position of the plunger 111 within the systolic-diastolic actuator, the purpose of which will be described further on in the text.

Each extension 113 and 115 is connected to a coil spring 117 and 119 respectively, which in turn is anchored to an anchor projection 121 at the end of the housing 97 in each bore 101 and 103 respectively. Within the central bore 99 and on the opposite side of the plunger 111 is a bellows 123 which is connected to the plunger 111 and to the systolic outlet port 125 of the housing 97. The satellite bores 101 and 103 each terminate in an open end defining diastolic ports 37 and 39 respectively. Within the satellite bores 101 and 103 are provided further bellows 127 and 129 as shown, which communicate with the diastolic ports 37 and 39.

As illustrated in FIG. 15, there is a plenum chamber 131 which extends through the housing 97 and communicates with the satellite bores 101 and 103. The function of the plenum chamber 131 is to dissipate air pressure within the satellite bores 101 and 103 as the bellows 127 and 129 are hydraulically expanded or contracted.

Referring to FIGS. 13 and 16, the operation of the systolic-diastolic actuator will now be described. On electrical stimulation of the pair of muscles 8 and 10, these muscles contract, the contractions forcing hydraulic fluid to be pumped from each of their attached pump drive units 3 into the hydraulic line 25, displacing fluid in the hydraulic line 25 into the bellows 109 and expanding the bellows longitudinally, thereby advancing the plunger 111 as well as the lateral extensions 113 and 115 thereof against the springs 117 and 119. As the plunger 111 advances, it contracts the bellows 123 in the central bore 99, forcing hydraulic fluid through the hydraulic line 33 and thereby expanding the driving bellows 95 of the blood pump 31. Expansion of the driving bellows 95 effects one systolic stroke of the blood pump 31, as will be described further on.

On completion of the systolic stroke, the electrical stimulation of the pair of muscles 8 and 10 is terminated by the control unit and the muscles relax. During diastole, the springs 117 and 119 will return the plunger 111 back to the end-diastolic position illustrated in FIG. 15, reversing the flow of fluid in the hydraulic line 33 and contracting the driving bellows 95 of the blood pump to its end-diastolic position, and reversing the flow of fluid in the hydraulic line 25 and lengthening the pump-drive units 3 attached to muscles 8 and 10 to their precontracted position.

If the duration of diastole must be shortened beyond that inherently provided by the coil springs 117 and 119, so as to increase the blood pump cycle rate during conditions such as strenuous exercise which require an increased blood pump output, the following response would be automatically effected. The electronic control system would stimulate the pair of muscles 21 and 23, each harnessed to a pump-drive unit 3, to contract. The contraction causes hydraulic fluid to be pumped from each of the pump-drive units into the hydraulic line 35, thereby displacing fluid through the diastolic ports 37 and 39, and expanding the bellows 127 and 129 which contact the plunger 111, hastening its movement to the end-diastolic position.

As described previously and illustrated in FIGS. 1 and 2, three other muscle pairs in addition to the pair of muscles 8 and 10 (FIG. 13) would be provided to power the systolic stroke, the hydraulic lines from these harnessed muscles being connected in a branch pattern to the line 25.

From calculation based on the actual size of the hydraulic components illustrated in FIG. 13, it is estimated that the hydraulic pressure in the hydraulic line 25 would be approximately 70 p.s.i. during a typical systolic stroke. It is anticipated that miniaturization of the pump-drive units, hydraulic lines, systolic-diastolic actuator and driving bellows 95 could be achieved with smaller volumes of hydraulic fluid in the respective components forced at higher pressures.

It is also anticipated that an access means to the systolic inlet port 27 may be provided to enable the blood pump to be temporarily powered by a hydraulic pump external to the subject, such a feature being deemed useful in the emergency installation of the heart replacement system.

In the embodiment shown in FIGS. 17 and 18, a hydraulic pressure reservoir unit 133 is schematically illustrated connected to the systolic-diastolic actuator 29. The hydraulic pressure reservoir unit 133 includes reservoirs 135 and 137 and a regulator 139 within a housing 141. A partition 143 separates the pressurized reservoir 135 from the return reservoir 137. The hydraulic pressure reservoir unit 133 is inserted in the hydraulic line 25, and as shown, hydraulic line segment 25a communicates with the inlet port 145. As hydraulic fluid in hydraulic line 25a is pressurized by contraction of the pump drive units, it opens the valve 147 and enters the pressurized reservoir 135 which includes an elastic membrane 149 separating the pressurized reservoir 135 from a gas-filled chamber 151. The return reservoir 137 is in communication with the hydraulic line 25a and includes a valve 153 which is open when hydraulic fluid is drawn towards the pump-drive units following contraction of these units.

The regulator 139 includes a valve block 155 which has a conduit 157 communicating with the pressurized reservoir 135. The conduit 157 intersects a valve bore 159 and communicates with the top of the valve bore 161. Fluid passing through the conduit 157 will expand the bellows 163 in the valve bore 161 against a spring 165.

A return conduit 167 extends from the valve bore 161 to drain fluid from within the bellows 163. The conduit 167 intersects the valve bore 159 and is in communication with the return reservoir 137. The sliding gate valve 169 is provided in the valve bore 159. The gate valve 169 includes an opening 171 which can alternatively open the communication through the conduits 157 or 167 respectively. A return spring 173 is provided at the end of the valve bore 159 to return the gate valve 169 to its initial position. A solenoid 175 operates the gate valve 169.

In the valve bore 161, a gate valve 177 is made to slide by means of the bellows 163 and is returned by the spring 165. The gate valve 177 has an opening 179 and a second spaced opening 181. The openings 179 and 181 are alternatively positioned to communicate with either the branch 183a or 183b of the outlet 183 in communication with the pressurized reservoir 135 or the return reservoir 137.

In operation, the pump drive units can, independently of the operation of the blood pump 31, build up the fluid pressure in the reservoir 135. To initiate systole of the blood pump 31, the solenoid 175 is operated such that the gate valve 169 is moved into a position where the opening 171 will be in line with the conduit 157 to allow fluid under pressure to enter the bellows 163, thus operating the gate valve 177 until the opening 179 is aligned with the branch 183a of the hydraulic line 25b, as shown in FIG. 18. Fluid under pressure in the pressurized reservoir 135 will then pass into the hydraulic line 25b, expanding the bellows 109 of the systolic-diastolic actuator 29.

In diastole, the spring 173 retracts the gate valve 169 to a position shown in FIG. 17, whereby the opening 171 is aligned with the conduit 167, blocking the conduit 157 and allowing fluid in the bellows 163 to be passed through the conduit 167 under compression of the bellows 163 by the spring 165, returning hydraulic fluid to the return reservoir 137. The spring 165 retracts the gate valve 177 such that branch 183a is blocked but opening 181 is aligned with the branch 183b in communication with the return reservoir 137. As previously described, spring devices in the pump-drive units would restore the pump-drive units to their pre-contracted length, drawing fluid from the return reservoir 137 past the valve 153.

In this embodiment, the muscles that are hydraulically harnessed to pressurize the reservoir 135 may contract slower than the stroke velocity of the blood pump 31. The frequency of contraction of these muscles is electronically determined from the pressure in the reservoir 135 by means of a pressure transducer (not shown).

In yet another embodiment shown in FIGS. 19 and 20, each pump drive unit 3 could be in communication with a device for converting the mechanical energy of muscle contraction into electrical energy and through an alternator to charge a battery for operating the electrical stimulation of the muscles harnessed with pump-drive units, and also for operating an electrically motorized blood pump. Such an embodiment would include the hydraulic line 61, communicating with the outlets 63 in the pump-drive unit 3. The hydraulic line 61 would in turn communicate with a closed circuit duct 185 which allows for one-way circulation of hydraulic fluid means of a valve 187. A dynamo 189 is inserted in the duct 185 upstream of a reservoir 191 which includes an elastic membrane 193. The dynamo 189 includes a hollow rotor 195 having a spiral rib 197. The rotor 195 includes a coil 199 which rotates in a conventional manner within a magnet 201. The current produced by the dynamo would then go to the alternator and battery as identified by the block 203.

When the pump-drive unit 3 is contracted by stimulated muscle contraction, fluid is moved through the hydraulic line 61 into the duct 185 and through the rotor 195 causing the rotor to rotate within the magnet 201, thereby converting the energy of muscle contraction into electrical energy. The fluid would then enter into the reservoir 191 against the elastic membrane 193. When the muscle 6 is relaxed, the pump-drive unit 3 is restored to its initial length by fluid flow effected by recoil of the membrane 193 and of the spring elements provided in the pump-drive unit.

Referring to FIGS. 21 to 32, the blood pump 31 includes a median partition 205 and a partition 207 within a housing 209. The partition 205 separates the blood pump into right and left halves. The partition 207 is oriented at right angles to partition 205 and separates each right and left half of the blood pump into a right ventricular chamber 211, a right atrial chamber 213, a left ventricular chamber 215, and a left atrial chamber 217, respectively.

A wedge 219 is hinged to the partition 207 by means of a hinge pin 221. As illustrated in FIGS. 21 and 25, the wedge 219 forms a wall of each of the chambers 211, 213, 215 and 217, so that pendulum motion of the wedge 219 about the hinge pin 221 during systole will expand each atrial chamber 213 and 217, and contract each ventricular chamber 211 and 215, while reverse movement of the wedge during diastole will contract each atrial chamber and expand each ventricular chamber.

A disc 223 is attached to the wedge 219 and rotates within a corresponding slot 225 in the partition 205 during pendulum motion of the wedge 219. The disc 223 functions as an extension of the partition 205.

A curved hollow cylinder 227 is attached to the wedge 219 by an extension 229 of the wedge. The cylinder 227 slides within a corresponding curved bore 231 provided in the housing 209 during pendulum motion of the wedge 219. The cylinder 227 is closed at one end 233, the other end being open. Within the cylinder is a driving bellows 95, one end of which is closed and attached to the closed end 233 of the cylinder 227, the other end being open and attached to the housing 209. As illustrated in FIG. 24, the driving bellows 95 communicates with the passage 235 in the housing 209, and thereby communicates with the hydraulic line 33.

Within each of the chambers 211, 213, 215, and 217, there is a bellows 237. Each bellows 237 has an open end attached to the housing 209 and to the partitions 205 and 207, and a closed end attached to a flap 239. Each flap 239 is hinged to the hinge pin 221 of partition 207 and may swing in a pivotal fashion independently of the wedge 219.

Figure 29:
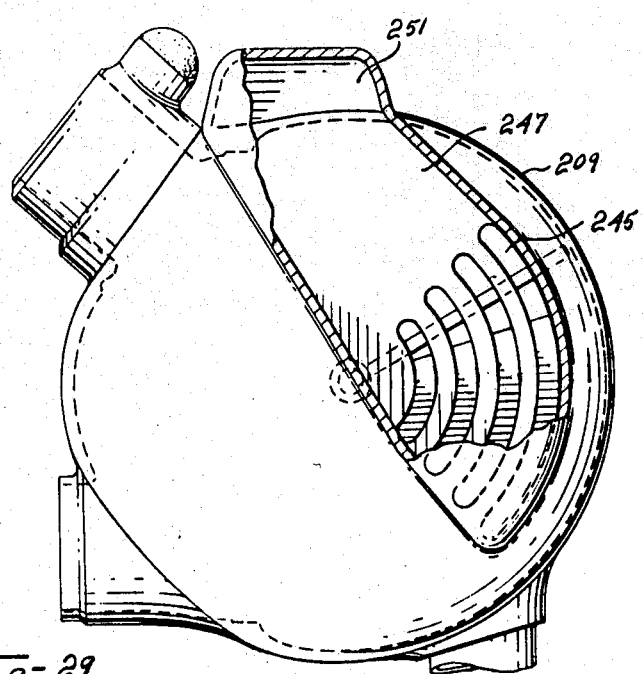
FIG. 29 is a side view of the blood pump, partly in section, taken through line 29—29 of FIG. 21.

Hydraulic fluid is provided between the wedge 219 and each of the flaps 239 and communicates with fluid between the exterior surface of each bellows 237 and the housing 209. The wedge 219 has a fluid filled core 241 which communicates by holes 243 in the wedge with the hydraulic fluid between each flap 239 and the wedge 219. The fluid core 241 extends within the left and right halves of the wedge 219. Thus, hydraulic fluid between the wedge 219 and flap 239 of any one chamber communicates with fluid in the corresponding spaces of the other three chambers. The fluid core 241 of the wedge 219 also communicates by holes 243 in the wedge 219 and holes 245 in the housing 209 with a fluid containing passage 247 and 249 in each left and right lateral aspect of the housing 209, as illustrated in FIG. 29. The two fluid passages 247 and 249 connect at a junction 251 and open into a hydraulic fluid reservoir 253 positioned between the left and right halves of the blood pump. An elastic membrane 255 forms the roof of the reservoir 253 and is attached to the exterior of the housing 209. The junction 251 also communicates with fluid within the curved bore 231 as illustrated in FIG. 24, so that fluid within the bore 231 is displaced into the junction 251 during systolic movement of the cylinder 227, and is drawn from the junction 251 into the bore 231 during diastolic movement of the cylinder 227.

Within each of the chambers 211, 213, 215, and 217 is a blood sac 257 attached at its open end to the housing 209, the partition 205 and the partition 207. The diameter of the open end of the blood sac 257 at its attachment is intended to be not greater than the sum of the diameters of the inlet and outlet blood passages of each chamber, to be described below, so that blood turbulence between the passages and the sac and within the sac is reduced and blood shear against the polyurethane-lined walls of the chamber space between the passages and the opening of the sac is also reduced.

Each blood sac 257 is suspended from its attached end in a fixed volume of hydraulic fluid 259 sealed within each of the bellows 237. The hydraulic fluid 259 will be referred to as a fluid cushion in that its function is to transmit pressure exerted by curvilinear expansion or contraction of the bellows 237 to the entire exterior surface of the blood sac, and also to separate the exterior surface of the blood sac from the interior surface of the bellows 237, the two surfaces being incongruous in structure.

The blood sac 257 is made of flexible, elastic polyurethane. Each blood sac is approximately conical in its contracted appearance, the base of the cone being the open end of the blood sac. Each blood sac 257 is molded in a corrugated pattern, the pattern consisting of two sets of corrugations. In the first set, the folds of the corrugations are aligned parallel to the circumferential axes of the cone. This set of corrugations facilitates longitudinal expansion of the blood sac. In the second set, the folds of the corrugations include the corrugations of the first set and span longitudinally from the base of the cone to the tip of the cone, as illustrated in FIG. 23. The second set of corrugations facilitates circumferential expansion of the blood sac.

The peaks and troughs of the folds in both sets of corrugations are rounded rather than jagged, the rounded nature of the peaks and troughs being less traumatic to the blood elements contained within the sac. The corrugated pattern of the blood sac combines the two sets of corrugations unequally so that longitudinal expansion predominates over circumferential expansion, and the proximal part of the blood sac adjacent to the open end expands in circumference less than the distal part. During expansion of the blood sac 257, the conical appearance is distorted into a hemi-ellipsoidal appearance as illustrated in FIG. 25.

Figure 32:
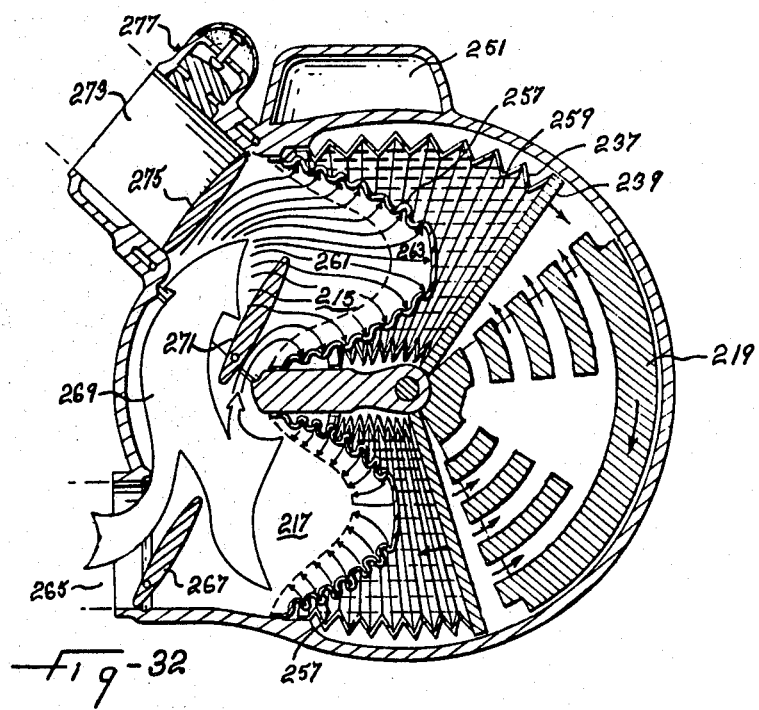
FIG. 32 is a cross-sectional view of the blodo pump similar to FIG. 25, the blood pump being shown in its mid-diastolic appearance.

The operation of the fluid cushion 259 and blood sac 257 will now be described for the left ventricular chamber 215, the operation being identical for the other three chambers. Referring to FIG. 32, curvilinear expansion of the bellows 237 in a pivotal fashion determined by the flap 239 negatively pressurizes the fluid cushion. The negative pressure of the fluid cushion is transmitted to the entire exterior of the sac 257 and thereby to the blood within the sac, causing blood to enter the sac 257 and expand the sac 257. As illustrated in FIG. 32, the fluid cushion 259 and the conical, corrugated construction of the blood sac 257 encourage specific flow characteristics of blood within the sac, such that the blood flow 261 in the main body of the expanding sac will be primarily parallel to the long axis of the sac, while the blood flow 263 adjacent to the walls of the sac will be primarily perpendicular to the wall of the sac.

These blood flow characteristics are maintained when the blood flow is reversed during contraction of the sac resulting from contraction of the bellows 237 and positive pressurization of the fluid cushion 259. These blood flow characteristics are beneficial in that shear flow of blood against the sac wall is lessened.

Figure 28:
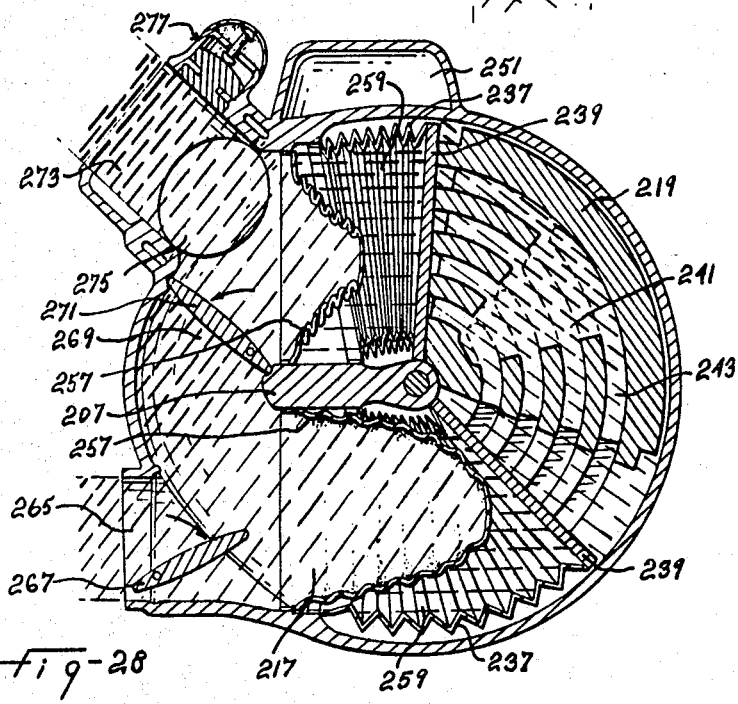
FIG. 28 is a cross-sectional view similar to FIG. 25, showing the blood pump in its end-systolic appearance.

Referring to FIGS. 25, 28 and 32, the left atrial chamber 217 communicates with a blood inflow passage 265 which is surgically connected to the pulmonary veins. The inflow passage 265 is provided with a tilting disc 267 which functions more as a flow guidance device than as a one-way valve. A blood outflow passage, the left atrial ventricular blood conduit 269, permits blood to flow from the left atrial chamber into the left ventricular chamber during diastole and is provided with a one-way tilting disc valve 271. The left ventricular chamber 215 communicates with a blood outlet passage 273 which is surgically connected to the aorta. The left ventricular blood outflow passage 273 is provided with an aortic tilting disc valve 275 and an aortic pressure transducer 277.

Figure 30:
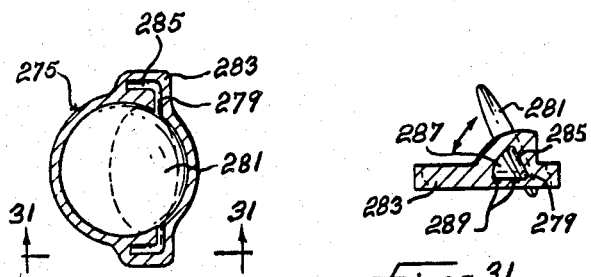
FIG. 30 is a cross-sectional view of an aortic valve taken through line 30—30 of FIG. 25.
Figure 31:
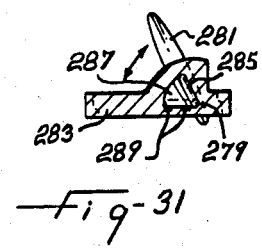
FIG. 31 is a cross-sectional view of the aortic valve taken through line 31—31 of FIG. 30.

As illustrated in FIGS. 30 and 31, the aortic disc valve 275 includes a hinge pin 279 attached to the tilting disc 281 and which articulates in a corresponding slot provided in the aortic valve housing 283. The disc 281 is ellipsoid in appearance, the ellipsoid design reducing flow turbulence around the disc. The hinge pin 279 has extensions 285 which move pivotally within wedge-shaped chambers 287 of the aortic valve housing 283. Each extension 285 abuts upon one face of the chamber 287 when the valve 275 is in its closed appearance, and abuts upon the opposite face of the chamber 287 when the valve is in its maximum open appearance, thus limiting the maximum opening of the valve. The aortic valve 275 differs from the other tilting disc valves in that electrical contacts 289 are provided in the face of each chamber 287 corresponding to the valve closed position. The electrical contacts 289 are closed by the extension 285 when the aortic valve is in its closed position, and opened when the aortic valve opens. The purpose of electronic sensing of aortic valve closing and opening will become apparent from the description of the electronic control system.

As illustrated in FIGS. 25 and 26, the aortic pressure transducer 277 includes a housing 291 and a polyurethane membrane 293 in a ring configuration attached to the housing 291. The membrane 293 separates blood within the ring from a fluid 295 outside the ring. The fluid 295 is sealed within the housing 291 between the membrane 293 and a second membrane 297 attached within the housing 291. A variable impedance device 299 is attached to the membrane 297 as is an electrical contact with a conducting arm 301 of the housing 291.

In operation, expansion or contraction of the ring membrane 293 will depend on the pressure of blood encircled by the membrane 293. Expansion or contraction of the ring membrane 293 will displace the fluid 295 and thereby bulge or depress respectively the membrane 297, resulting in vertical travel of the variable impedance device 299. Vertical travel of the variable impedance device 299 against the contact arm 301 will vary the current flowing through the variable impedance device and conducted to the electronic control system.

The arrangement of the right half of the blood pump is similar to the left half just described with the exception of the following. The right atrial inflow passage is surgically connected to the vena cavae, and the right ventricular outflow passage is surgically connected to the pulmonary artery. The right ventricular outflow passage has no pressure transducer.

Referring to FIGS. 24, 25, 27 and 28, the general operation of the blood pump 31 will now be described. Displacement of fluid from the hydraulic line 33 into the driving bellows 95 during systole (at approximately 40 p.s.i.) expands the bellows 95. Expansion of the bellows 95 moves the cylinder 227 and the attached wedge 219 pivotally around the hinge pin 221, expanding the left and right atrial chambers and contracting the left and right ventricular chambers. Expansion of the left atrial chamber 217 negatively pressurizes (approximately −5 to −15 mm Hg) the fluid between the wedge 219 and the left atrial bellows flap 239, expanding the bellows 237 and the left atrial blood sac 257.

The negative pressure of the fluid space between the left atrial flap 239 and the wedge 219 is dampened by flow of additional fluid into this space. This additional fluid is drawn from the fluid space between the left ventricular bellows flap and the wedge through the holes 243 in the wedge, and also from the bore 231 and from the reservoir 253 against the elastic recoil of the membrane 255. The expansion of the fluid space between the wedge 219 and the left atrial flap 239 dampens the pressure exerted on the blood within the left atrial sac 257 and thereby dampens the pressure exerted within the inflow passage 265 on the pulmonary veins. The degree of expansion of the fluid space between the wedge 219 and the left atrial flap 239 depends inversely on the pressure of blood within the pulmonary veins and varies inversely with the degree of filling of the left atrial blood sac during systole.

The pressure gradient between blood in the pulmonary veins and blood in the left atrial chamber results in blood flow from the pulmonary veins through the inflow passage 265 into, and expanding, the left atrial sac 257.

Expansion of the right atrial chamber 213 similarly expands the right atrial blood sac with blood from the vena cavae.

Contraction of the left ventricular chamber 215 positively pressurizes the fluid between the wedge 219 and the left ventricular bellows flap 239. The positive pressure displaces this fluid through the holes 243 in the wedge 219 and into the corresponding fluid space of the left atrial chamber 217. The wedge 219 then abuts upon the left ventricular bellows flap 239 and further systolic movement of the wedge 219 positively pressurizes (to approximately 140 mm Hg) the cushion fluid 259 within the left ventricular bellows 237. The blood sac 257 of the left ventricular chamber is thereby pressurized and blood flows from within the left ventricular blood sac through the left ventricular outflow passage 273 and into the aorta down a pressure gradient (approximately 30 to 50 mm Hg) between the pressurized left ventricular sac and the aorta, closing the valve 271 and opening the aortic valve 275.

Contraction of the right ventricular chamber similarly pressurizes (to approximately 50 mm Hg) the right ventricular blood sac and causes blood to flow into the pulmonary artery.

In diastole, fluid is drawn from the driving bellows 95 into the hydraulic line 33 by recoil of the springs 117 and 119 in the systolic-diastolic actuator 29. The driving bellows 95 is thereby contracted and pulls the cylinder 227 and attached wedge 219 pivotally around the hinge pin 221, contracting the left and right atrial chambers 217 and 213 and expanding the left and right ventricular chambers 215 and 211.

Contraction of the left atrial chamber 217 increases the pressure of the fluid between the wedge 219 and the left atrial flap 239 and displaces this fluid into the corresponding fluid space of the left ventricular chamber and into the expanding volume of the bore 231 and into the reservoir 253 via the passage 249. During diastole, the bore 231 is completely reexpanded and the reservoir 253 is at least partially re-expanded by recoil of the elastic membrane 255, the degree of re-expansion of the reservoir 253 depending directly on the pressure of blood within the pulmonary veins. Consequently, the potential expansion of the left ventricular blood sac during diastole is greater than the expansion of the left atrial blood sac during systole.

Synchronous with the displacement of hydraulic fluid from the left atrial chamber during diastole, the left atrial blood sac is similarly pressurized and contracts, causing blood to flow from the left atrial sac through the left atrial-ventricular blood conduit 269 into the left ventricular chamber, opening the valve 271.

Expansion of the left ventricular chamber 215 during diastole negatively pressurizes the left ventricular chamber with respect to the left atrial chamber and the pulmonary veins. As illustrated in FIG. 32, the left ventricular blood sac expands with blood flowing from both the left atrial chamber and from the pulmonary veins. This is made possible by the potential expansion of the left ventricular blood sac being greater than the expansion of the left atrial blood sac, as described above, and by the diastolic pressure within the left ventricular chamber being generally lower than the pressure of blood within the pulmonary veins. Thus, blood flow from the pulmonary veins into the left half of the blood pump begins with the beginning of systole and may continue throughout diastole.

The operation of the right half of the blood pump during diastole is similar to that described for the left half.

The function of the reservoir 253 can now be summarized. As described above, reservoir fluid is drawn from the reservoir 253 against the membrane 255 into the atrial chambers during systole to dampen the pressure transmitted to blood within the atrial chambers and veins supplying the atrial chambers. Under conditions of normal pressure of blood within the veins, the reservoir fluid is returned to the reservoir 253 during diastole by elastic recoil of the membrane 255. Under conditions of reduced pressure in the veins supplying either one or both halves of the blood pump, the reservoir fluid may be retained in either one or both halves of the blood pump, the amount of fluid being retained depending inversely on the pressure of blood within the veins supplying either one or both halves of the blood pump and resulting in reduced filling of either one or both halves of the blood pump with blood. This results in a reduced systolic blood stroke volume in either one or both halves of the blood pump.

Under conditions of normal pressure of blood within the veins and with the reservoir 253 replenished during diastole, each half of the blood pump contains fluid between the bellows flaps 239 and the wedge 219 equivalent in amount to 12% of the normal end-diastolic blood volume of each ventricular blood sac. Under conditions where the pressure of blood in the veins supplying one half of the blood pump exceeds the pressure of blood in the veins supplying the other half of the blood pump, this fluid may flow from that half of the blood pump experiencing the higher venous pressure to that half of the blood pump experiencing the lower venous pressure through the core 241 in the wedge 219 providing communication between the two halves of the blood pump. This results in as much as a 12% reduction in blood filling of that half of the blood pump experiencing the lower venous pressure and in as much as a 12% increase in blood filling of that half of the blood pump experiencing the higher venous pressure. Thus, the systolic blood stroke volume of that half of the blood pump experiencing the lower venous pressure may be reduced as much as 12%, while the systolic blood stroke volume of that half of the blood pump experiencing the higher venous pressure may be increased as much as 12%, thereby augmenting the flow of arterial blood to that half of the vascular system (systemic or pulmonic) which has the lower venous pressure. This mechanism operates according to the discrepancy in venous pressures experienced by the left and right halves of the blood pump, and operates independently of the function of the fluid reservoir 253.

It is anticipated that the atrial bellows, flaps, and chambers could be constructed smaller than the ventricular bellows, flaps and chambers as an adjunctive means of assuring that atrial blood filling during systole is less than ventricular blood filling during diastole.

It is also anticipated that the fluid reservoir 253 could be located outside the chest in the abdominal wall, connected appropriately by a hydraulic line to the blood pump, so that the pressure sensitive membrane 255 of the fluid reservoir would be isolated from the changes in intrathoracic pressure that occur with breathing.

Referring to FIG. 33, the electronic muscle stimulation and blood pump control system comprises a clock 303, an electromechanical synchronizer (EMS) 305, a central processing unit (CPU) 307, and a sequencer 309. The electronic system is powered by a lithium 3-volt battery 311 and is unipolar, the subject's body acting as ground. The various electronic components except the clock and battery, would be embodied in appropriately programmed microprocessors.

The clock 303 shapes the current from the battery 311 into 0.3 m sec 3-volt pulses of frequency 1000 Hz, as illustrated in FIG. 34, and establishes a minimum blood pump cycle rate of one per second.

The EMS 305 synchronizes muscle stimulation with plunger travel of the systolic-diastolic actuator 29, which is provided with electrical contacts 119 as previously described. The electrical output of the systolic-diastolic actuator is also fed to the CPU 307. The CPU includes an electrical pulse frequencer which shapes the pulses of the clock into a programmed decreasing frequency (60→20 Hz) for stimulation of a muscle pair during systole. An example of the pulse pattern so produced is illustrated in FIG. 35 for normal aortic pressure and left sided venous pressure indices.

Aortic pressure measurement is electronically determined directly from the aortic pressure transducer 277. Left sided venous pressure measurement is derived indirectly from electronic measurement of the distance travelled during systole by the plunger 111 of the systolic-diastolic actuator 29 prior to opening of the contact 289 of the aortic valve 275 indicating opening of the aortic valve. As described previously, the amount of fluid drawn from the reservoir 253 of the blood pump into the left ventricular chamber during diastole depends inversely on the pressure of blood within the pulmonary veins. During systole, this fluid is displaced from the left ventricular chamber prior to opening of the aortic valve. Thus, the distance travelled during systole by the plunger 111 from its end-diastolic position to the position, as measured by the sensor contacts 114, corresponding to the moment of opening of the aortic valve, depends inversely on the pressure of blood within the pulmonary veins.

The CPU 307 integrates the aortic pressure and left sided venous pressure indices and acts on the electrical pulse frequencer to alter the frequency and duration of the muscle stimulating pulse pattern in order to maintain these indices within normal range. For example, if the aortic pressure falls or left sided venous pressure rises out of normal range, the pulse pattern stimulating contraction of a muscle pair during systole would be shortened and intensified in order to shorten systole, and the muscle pair 22 harnessed to assist recoil of the springs 117 and 119 of the systolic-diastolic actuator would be stimulated to shorten diastole. An example of the pulse pattern so produced is illustrated in FIG. 36.

The sequencer 309 alternates the systolic electrical pulse waves of the electrical pulse frequencer to the four muscle pairs 6, 10, 14 and 18 powering systole, so that each muscle pair contracts for one of four consecutive systolic strokes and contracts in a sequence with the other three muscle pairs. It is contemplated that the CPU 307 will possess a memory feature enabling the CPU to individualize the pulse frequencer output for each muscle pair depending on the sensory indices of prior stroke cycles corresponding to each muscle pair.

It is also contemplated that the electrical system will include a telemetric sensor and transmitter 313. This will enable an external programmer to monitor the indices pertaining to operation of the blood pump, and to non-invasively reprogram the sensitivity of the CPU to these indices to compensate for transducer drift and subject variability.

I claim:
1. Apparatus for use in a heart replacement blood pump comprising a plurality of actively pumping chambers, each of the chambers including side walls and a reciprocating moving wall, an expandable sealed chamber in each pump chamber attached to side walls thereof and to the movable reciprocating wall and containing a hydraulic fluid forming a cushion, a blood sac in each pumping chamber having an open end attached to the side walls thereof and being fully supported towards and including its closed end by the cushion formed by the hydraulic fluid, the blood sac being somewhat conical when in a collapsed position and hemi-ellipsoidal shape when in an extended position, the blood sac being molded in a corrugated pattern consisting of elongated corrugations extending in its longitudinal direction and annular corrugations extending circumferentially of the sac, such that the sac can expand circumferentially and longitudinally when drawn by the cushion acting on the sac under the influence of negative pressure to expand the sac and thus causing blood to enter the sac.

2. An artificial replacement muscle in combination with an implatable motive power apparatus, comprising means for harnessing the contractile force of one or more skeletal muscles while the skeletal muscles remain in their anatomic position, and means for transmitting the motive power from said means for harnessing to the artificial replacement muscle for operating the artificial muscle in a manner simulating the operation of the muscle it is replacing, wherein the means for harnessing a skeletal muscle includes a linear displacement hydraulic motor having anchor plates at each end thereof respectively adapted to be connected to the tendon material at each end of the muscle, and hydraulic fluid displacement means associated with the motor for displacing hydraulic fluid when the skeletal muscle contracts, wherein the artificial replacement muscle is a heart pump and the harness means are individually adapted to be attached to a plurality of skeletal muscles and the respective insertion tendons of said skeletal muscles are severed, and the natural motor nerves of the skeletal muscles are sugically interrupted, and the anchor plates of said harness means are adapted to be connected to each end of the respective muscle, and artificial stimulation means are provided such that the harnessed muscles will contract in sequence, wherein a systolic-diastolic actuator is provided and is implantable within the body, and said hydraulic conduit extends from each hydraulic motor means to one end of the systolic-diastolic actuator and a single conduit means extends from the systolic-diastolic actuator to the blood pump, each pulse of hydraulic pressure from the hydraulic motor means adapted to be attached to said skeletal muscles in response to said sequential contraction of said muscles causing the systolic-diastolic actuator to transmit through said single hydraulic line hydraulic pressure to the heart pump to power corresponding systolic strokes of the blood pump, wherein the systolic-diastolic actuator includes a housing defining a central bore passing through the housing, an inlet at one end of the housing communicating with the bore and an outlet at the other end of the housing communicating with the bore, a plunger being slidable within the bore and a sealed expandable chamber being provided within the bore communicating with the inlet and abutting the plunger, a sealed expandable chamber provided in the bore communicating with the outlet, and hydraulic fluid conduits from the varius hydraulic bores communicating with the inlet of the bore, whereby when hydraulic fluid from one of said hydraulic motors is displaced upon contraction of a muscle, the fluid pressure in the hydraulic conduits will expand the sealed chamber within the bore communicating with the inlet, thereby moving the plunger towards the outlet and thereby displacing the hydraulic fluid to the heart pump to effect the systolic stroke, and means for returning the plunger to its initial position during diastole; a parallel satellite bore extending adjacent the said bore and the plunger has an extension which extends laterally into the satellite bore, an inlet port provided on the housing communicating with the satellite bore but adjacent and on the same side as the outlet of the central bore, an expandable sealed chamber provided in the satellite bore communicating with the inlet and contacting the extension of the plunger, harness means and a hydraulic conduit communicating with the inlet port of the satellite bore such that when the muscle to which the latter harness means is attached is stimulated, it will dispace hydraulic fluid through the hydraulic conduit into the satellite bore through the inlet port thereby efflectively hastening diastolic stroke when necessary; electrical sensor members provided in the housing, and electrical contact means on said plunger adapted to slide against said sensor members in order to electronically sense the position of the plunger within the systolic-diastolic actuator.

3. An apparatus as defined in claim 2 wherein a reservoir for hydraulic fluid is provided in the conduits between the plurality of hydraulic motors, and the inlet port to the central bore of the systolic-diastolic actuator means such that hydraulic fluid can be displaced into the reservoir and the hydraulic pressure can be stored in response to the contraction of the respective muscles and the displacement of the fluid towards the reservoir, and valve means for providing a regualted pulse of hydraulic pressure to the systolic-diastolic actuator means; the reservoir including a chamber adapted to receive the hydraulic fluid and having an elastic membrane separating the chamber between a gas filled sub-chamber and a hydraulic fluid sub-chamber, said valve means including a solenoid operated valve controlled by control means for opening and closing the valve to allow fluid from the hydraulic fluid sub-chamber to the inlet of the central bore in the systolic-diastolic actuator means and a position whereby communication between the hydraulic fluid sub-reservoir and the inlet is blocked off and the return from the inlet is passed through a return reservoir during diastole.

4. An apparatus as defined in claim 2 wherein spring means are fixed at one end to the housing and at the other end to the plunger so as to return the plunger during diastole to its end-diastolic position forcing the hydraulic fluid from the expandable chamber to return to the hydraulic motor means, thereby extending the respective muscles to their relaxed position.

5. An artificial replacement muscle in combination with an implantable motive power apparatus, comprising means for harnessing the contractile force of one or more skeletal muscles while the skeletal muscles remain in their anatomic position, and means for transmitting the motive power from said means for harnessing to the artificial replacement muscle for operating the artificial muscle in a manner simulating the operation of the muscle it is replacing, wherein the means for harnessing a skeletal muscle includes a linear displacement hydraulic motor having anchor plates at each end thereof respectively adapted to be connected to the tendon material at each end of the muscle, and hydraulic fluid displacement means associated with the motor for displacing hydraulic fluid when the skeletal muscle contracts, wherein the hydraulic motor includes a pair of elongated sealed expandable chambers connected in parallel at each end to respective anchor plates, and guide means enable the hydraulic motor to expand and contract along a linear path longitudinally of the muscle.

6. An apparatus as defined in claim 5, wherein the hydraulic motor includes at least one anchor means which is pivotally connected to the remainder of the hydraulic motor means in order to provide more flexible movement to the muscle to which the hydraulic motor means is to be harnessed.

7. An artificial replacement muscle in combination with an implantable motive power apparatus, comprising means for harnessing the contractile force of one or more skeletal muscles while the skeletal muscles remain in their anatomic position, and means for transmitting the motive power from said means for harnessing to the artificial replacement muscle for operating the artificial muscle in a manner simulating the operation of the muscle it is replacing, wherein the means for harnessing a skeletal muscle includes a linear displacement hydraulic motor having anchor plates at each end thereof respectively adapted to be connected to the tendon material at each end of the muscle, and hydraulic fluid displacement means associated with the motor for displacing hydraulic fluid when the skeletal muscle contracts, wherein the artificial replacement muscle is a heart pump and the harness means are individually adapted to be attached to a plurality of skeletal muscles and the respective insertion tendons of said skeletal muscles are severed, and the natural motor nerves of the skeletal muscles are surgically interrupted, and the anchor plates of said harness means are adapted to be connected to each end of the respective muscle, and artificial stimulation means are provided such that the harnessed muscles will contract in sequence, wherein the anchor plates include small arrow-shaped anchor elements adapted to pierce and engage in the tendon material to which the plate is being anchored, and openings provided in a zigzag pattern along an axis at right angles to the tendon fiber alignment of the muscle, the openings being interspaced between the anchor elements and the openings being sufficient to allow suture material to be passed therethrough into the tendon material; the subsequent biological transformation of the suture material into fibrous tissue results in binding of the anchor plate to the tendon material in such a way that the fibrous tissue is aligned between the anchor elements in general alignment normal to the tendon fiber alignment.

8. An artificial replacement muscle in combination with an implantable motive power apparatus, comprising means for harnessing the contractile force of one or more skeletal muscles while the skeletal muscles remain in their anatomic position, and means for transmitting the motive power from said means for harnessing to the artificial replacement muscle for operation the aritificial muscle in a manner simulating the operation of the muscle it is replacing, wherein the means for harnessing a skeletal muscle includes a linear displacement hydraulic motor having anchor plates at each end thereof respectively adapted to be connected to the tendon material at each end of the muscle, and hydraulic fluid displacement means associated with the motor for displacing hydraulic fluid when the skeletal muscle contracts, wherein the hydraulic pressure from the hydraulic motor effected by contraction of the harnessed muscle is connected to means for converting said pressure into electrical power.

9. An apparatus as defined in claim 8, wherein the hydraulic conduit from the hydraulic motor means to be harnessed to the muscle forms a closed circuit and a dynamo means is provided in the closed circuit whereby, as the muscle is contracted, the dynamo is forced to rotate by the hydraulic fluid pressure, thereby producing electricity.

10. An apparatus as defined in claim 9, wherein the closed circuit is unidirectional and a one-way valve prevents backflow of the hydraulic fluid, a pressure chamber is provided in the closed circuit line downstream of the dynamo, the pressure chamber including an elastic membrane adapted to be extended against a compressible fluid trapped behind the membrane thereby effecting an accumulated pressure for returning the fluid to the hydraulic motor in order to extend the muscle to its relaxed position.

11. An artificial replacement muscle in combination with an implantable motive power apparatus, comprising means for harnessing the contractile force of one or more skeletal muscles while the skeletal muscles remain in their anatomic position, and means for transmitting the motive power from said means for harnessing to the artificial replacement muscle for operating the artificial muscle in a manner simulating the operation of the muscle it is replacing, wherein the means for harnessing a skeletal muscle includes a linear displacement hydraulic motor having anchor plates at each end thereof respectively adapted to be connected to the tendon material at each end of the muscle, and hydraulic fluid displacement means associated with the motor for displacing hydraulic fluid when the skeletal muscle contracts, wherein said means for transmitting the motive power includes a conduit means for passing the hydraulic fluid and dynamo means interrupting said conduit means for converting the hydraulic pressure into electricity, and means for storing said electricity.

12. A heart replacement blood pump comprising four actively pumping chambers, two of the chambers simulating ventricles and two of the chambers simulating atria, wherein the ventricular and atrial chambers are driven reciprocally by a hydraulic motor, the four chambers being formed by the intersection of first and second partitions at right angles to each other, inlet ports are provided respectively to each of the atrial chambers and outlet ports are provided respectively to the ventricular chambers while passage means are piovided between each respective atrial chamber and ventriclular chamber, wherein the atrial chambers are actively pumping chambers as well as the ventricular chambers so as to enable venous uptake by the blood pump to occur throughout systole and into daistole but ejection of blood into the arteries occurs only during systole, wherein the hydraulic motor includes a wedge member, the apex of which is hinged to the first partition, said wedge having surfaces forming a movable wall of each of the four respective chambers such that the pendulum motion of the wedge about its hinged axis during systole will expand each atrial chamber and contract each ventricular chamber and reverse movement of the wedge during diastole will contract each atrial chamber and expand each ventricular chamber.

13. A blood pump as defined in claim 12 wherein a curved bore is provided in the housing of the blood pump with its central axis in the plane of the second partition, a curved cylinder is fixed to the wedge and adapted to slide in the curved bore, a disc concentric with the hinge axis of the wedge and in the plane of the second partition is fixed to the curved cylinder, one end of said bore being an inlet adapted to communicate with a hydraulic motive source, an expandable sealed chamber communicating with said inlet and extending within said curved bore and abutting the curved cylinder whereby, when the fluid pressure is exerted within the expandable chamber, the curved cylinder will be displaced within the bore, thereby moving the wedge fixed thereto effecting systole.

14. A blood pump as defined in claim 12, wherein the four respective chambers include two pairs of chambers, each pair having an atrial chamber and a ventricular chamber, the first pair simulating the left half of a heart and the second pair simulating the right half of a heart; the surfaces of the wedge forming the respective movable walls of the respective chambers are in the form of independently hinged flaps on either side of the wedge, the wedge being fenestrated and having through passages communicating each side of the wedge, passage means communicating the wedge from the first pair to the second across the second partition, hydraulic fluid in the wedge spaces filling the fenestrations and passages, a predetermined amount of excess hydraulic fluid in the wedge spaces sufficient to maintain a combined wedge space volume greater than the volume of the wedges such that when conditions where the pressure of blood in the veins supplying one pair of chambers exceeds the pressure of blood in the veins supplying the other pair of chambers, the hydraulic fluid will flow from the wedge space corresponding to the one pair of chambers to the wedge space corresponding to the other pair of chambers experiencing the lower venous pressure, thereby resulting in a reduction in blood filling in the other pair of chambers experiencing the lower venous pressure and an increase in blood filling in the one pair of chambers experiencing the higher venous pressure, thus reducing the effective blood stroke volume of the other pair of chambers experiencing the lower venous pressure while the effective blood stroke volume of the one pair of chambers experiencing the higher venous pressure may be increased a corresponding amount, thereby augumenting the flow of arterial blood to the other pair of chambers which has the lower venous pressure.

15. A blood pump as defined in claim 14 wherein fluid reservoir means are provided to communicate with the wedge spaces such that fluid can be drawn into the wedge spaces between the respective flaps, the reservoir including an elastic membrane, whereby fluid will be drawn into the wedge space between the flaps against the membrane, thereby dampening the pressure exerted on the blood within the chambers of respective pairs of chambers, the degree of expansion of the wedge fluid space between the flaps between either pair of chambers being inversely proportional to respective venous pressures.

* * * * *